United States Patent
Whitaker et al.

(10) Patent No.: US 7,651,559 B2
(45) Date of Patent: *Jan. 26, 2010

(54) MINERAL COMPOSITION

(75) Inventors: Robert H. Whitaker, Cleveland, GA (US); Richard Brann, Franklin, TN (US)

(73) Assignee: Franklin Industrial Minerals, Brentwood, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/999,205

(22) Filed: Dec. 4, 2007

(65) Prior Publication Data

US 2008/0173212 A1 Jul. 24, 2008

Related U.S. Application Data

(63) Continuation-in-part of application No. 11/638,618, filed on Dec. 13, 2006, which is a continuation-in-part of application No. 11/266,833, filed on Nov. 4, 2005.

(51) Int. Cl.
*C09D 4/00* (2006.01)

(52) U.S. Cl. .............................. 106/284.04; 106/18.36; 106/15.05; 106/285; 106/738; 106/817; 523/122; 428/143

(58) Field of Classification Search .................. 428/143; 106/18.36, 15.15, 284.04, 285, 738, 817; 523/122

See application file for complete search history.

(56) References Cited

U.S. PATENT DOCUMENTS

| | | | |
|---|---|---|---|
| 2,369,125 A | 2/1945 | Anderson | |
| 2,469,728 A | 5/1949 | Holmes | |
| 2,572,086 A | 10/1951 | Wittcoff | |
| 2,582,823 A | 1/1952 | Fowkes | |
| 2,582,824 A | 1/1952 | Fowkes | |
| 2,590,910 A | 4/1952 | Wittcoff | |
| 2,729,660 A | 1/1956 | Harrison | |
| 3,373,812 A | 3/1968 | Smith | |
| 3,420,231 A | 1/1969 | Edenbaum | |
| 3,490,039 A | 1/1970 | Tsao | |
| 3,519,452 A | 7/1970 | Rivin | |
| 3,557,040 A | 1/1971 | Takashina | |
| 3,563,916 A | 2/1971 | Takashina | |
| 3,601,376 A | 8/1971 | Niemitz | |
| 3,608,841 A | 9/1971 | Wageneder | |
| 3,615,329 A | 10/1971 | Jones | |
| 3,617,329 A | 11/1971 | Goff | |
| 3,617,560 A | 11/1971 | Deul | |

(Continued)

FOREIGN PATENT DOCUMENTS

WO  WO-9745607  12/1997

*Primary Examiner*—Holly Rickman
*Assistant Examiner*—Linda Chau
(74) *Attorney, Agent, or Firm*—Howard J. Greenwald

(57) ABSTRACT

A mineral composition comprised of at least about 90 weight percent of roofing granules, at least about 50 weight percent of calcium carbonate with a hardgrove grindability index of less than about 70, from about 0.1 to about 1.0 weight percent of a pigmented material, from about 0.1 to about 1.0 weight percent of a composition for inhibiting the growth of an organism selected from the group consisting of algae, bacteria, and mixtures thereof, and less than about 100 parts per million of a metal selected from the group consisting from the group consisting of arsenic, barium, cadmium, chromium, lead, mercury, selenium, and silver, and less than about 100 parts per million of a polycyclic aromatic hydrocarbon. The mineral composition, when tested in accordance with by ASTM Standard Test D 4977-03, loses less than 5 grams of material.

4 Claims, 3 Drawing Sheets

U.S. PATENT DOCUMENTS

| | | |
|---|---|---|
| 3,722,867 A | 3/1973 | Butler |
| 3,725,103 A | 4/1973 | Jordan |
| 3,737,678 A | 6/1973 | Dolby |
| 3,737,704 A | 6/1973 | Grenon |
| 3,772,857 A | 11/1973 | Jackson |
| 3,775,984 A | 12/1973 | Livingston |
| 3,780,012 A | 12/1973 | Smith |
| 3,780,013 A | 12/1973 | Smith |
| 3,799,788 A | 3/1974 | Jordan |
| 3,833,541 A | 9/1974 | Shen |
| 3,836,378 A | 9/1974 | Hahnkamm |
| 3,839,064 A | 10/1974 | Vincent |
| 3,849,927 A | 11/1974 | Gonsalves |
| 3,874,444 A | 4/1975 | Perce |
| 3,877,454 A | 4/1975 | Axmann |
| 3,881,708 A | 5/1975 | Carle |
| 3,884,706 A | 5/1975 | Little |
| 3,888,684 A | 6/1975 | Little |
| 3,900,434 A | 8/1975 | Bruschtein |
| 3,901,836 A | 8/1975 | Kader |
| 3,919,163 A | 11/1975 | Clendinning |
| 3,921,358 A | 11/1975 | Bettoli |
| 3,925,095 A | 12/1975 | Bockmann |
| 3,925,301 A | 12/1975 | Engel |
| 3,930,101 A | 12/1975 | Vincent |
| 3,938,469 A | 2/1976 | Nau |
| 3,947,246 A | 3/1976 | Eibl |
| 3,962,072 A | 6/1976 | Ramacher |
| 3,973,983 A | 8/1976 | Jordan |
| 3,980,448 A | 9/1976 | Haemmerle |
| 3,995,079 A | 11/1976 | Haas, Jr. |
| 4,013,617 A | 3/1977 | Gordon |
| 4,015,973 A | 4/1977 | Perrine |
| 4,017,433 A | 4/1977 | Farrington |
| 4,026,763 A | 5/1977 | Poindexter |
| 4,038,102 A | 7/1977 | Hellsten |
| 4,075,029 A | 2/1978 | Nuss |
| 4,076,551 A | 2/1978 | Bernhard |
| 4,087,479 A | 5/1978 | Toyota |
| 4,092,441 A | 5/1978 | Meyer |
| 4,101,429 A | 7/1978 | Birke |
| 4,116,488 A | 9/1978 | Hsueh |
| 4,134,619 A | 1/1979 | Bunnelle |
| 4,167,417 A | 9/1979 | Franz |
| 4,170,486 A | 10/1979 | Doppler |
| 4,172,070 A | 10/1979 | Scharrer |
| 4,174,974 A | 11/1979 | Fondriest |
| 4,180,466 A | 12/1979 | Newingham |
| 4,189,184 A | 2/1980 | Green |
| 4,198,097 A | 4/1980 | Fondriest |
| 4,202,702 A | 5/1980 | Nuss |
| 4,231,884 A | 11/1980 | Dorius |
| 4,237,025 A | 12/1980 | Tadros |
| 4,239,736 A | 12/1980 | Fenske |
| 4,242,475 A | 12/1980 | Tsuchiya |
| 4,269,760 A | 5/1981 | Wakimoto |
| 4,272,498 A | 6/1981 | Faatz |
| 4,274,243 A | 6/1981 | Corbin |
| 4,288,162 A | 9/1981 | Sakamoto |
| 4,293,478 A | 10/1981 | Sugio |
| 4,316,813 A | 2/1982 | Voss |
| 4,323,281 A | 4/1982 | Greenwald, Sr. |
| 4,324,453 A | 4/1982 | Patel |
| 4,328,147 A | 5/1982 | Chang |
| 4,329,179 A | 5/1982 | Kutta |
| 4,334,933 A | 6/1982 | Abe |
| 4,349,389 A | 9/1982 | Schofield |
| 4,352,837 A | 10/1982 | Kopenhaver |
| 4,356,572 A | 11/1982 | Guillemin |
| 4,358,415 A | 11/1982 | Tachimoto |
| 4,359,505 A | 11/1982 | Joedicke |
| 4,366,138 A | 12/1982 | Eisenmenger |
| 4,374,168 A | 2/1983 | Wojtowicz |
| 4,374,645 A | 2/1983 | Monteyne |
| 4,379,871 A | 4/1983 | Werle |
| 4,382,989 A | 5/1983 | Chang |
| 4,390,349 A | 6/1983 | Jen-Tung |
| 4,402,881 A | 9/1983 | Alther |
| 4,419,456 A | 12/1983 | Audeh |
| 4,420,445 A | 12/1983 | Yamamoto |
| 4,425,057 A | 1/1984 | Hahn |
| 4,428,850 A | 1/1984 | Zoleski |
| 4,430,127 A | 2/1984 | Dalter |
| 4,430,281 A | 2/1984 | Boylan |
| 4,442,160 A | 4/1984 | Toba |
| 4,447,269 A | 5/1984 | Schreuders |
| 4,452,961 A | 6/1984 | Koerner |
| 4,462,840 A | 7/1984 | Schilling |
| 4,486,476 A | 12/1984 | Fritsch |
| 4,510,062 A | 4/1985 | Nakanishi |
| 4,521,278 A | 6/1985 | Kelley |
| 4,528,363 A | 7/1985 | Tominaga |
| 4,530,924 A | 7/1985 | Polony |
| 4,537,595 A | 8/1985 | Gruning |
| 4,548,746 A | 10/1985 | Duncan |
| 4,576,638 A | 3/1986 | Doerr |
| 4,594,236 A | 6/1986 | Eriksson |
| 4,613,084 A * | 9/1986 | Takamoto et al. ............. 241/16 |
| 4,614,755 A | 9/1986 | Rodgers |
| 4,629,130 A | 12/1986 | Veltman |
| 4,629,506 A | 12/1986 | Ulrich |
| 4,634,622 A | 1/1987 | Jenkins |
| 4,662,915 A | 5/1987 | Shirai |
| 4,671,208 A | 6/1987 | Smith |
| 4,676,917 A | 6/1987 | Sung |
| 4,683,158 A | 7/1987 | Yasuoka |
| 4,699,429 A | 10/1987 | Maybrier |
| 4,710,226 A | 12/1987 | Mallow |
| 4,717,614 A | 1/1988 | Bondoc |
| 4,720,350 A | 1/1988 | Zoleski |
| 4,721,159 A | 1/1988 | Ohkochi |
| 4,721,529 A | 1/1988 | Mullins |
| 4,734,450 A | 3/1988 | Kawai |
| 4,736,311 A | 4/1988 | Takeuchi |
| 4,738,884 A * | 4/1988 | Algrim et al. ................. 428/57 |
| 4,742,718 A | 5/1988 | Jimbo |
| 4,758,260 A | 7/1988 | Geropp |
| 4,781,759 A | 11/1988 | Smith |
| 4,781,846 A | 11/1988 | Kanamori |
| 4,781,950 A | 11/1988 | Giesing |
| 4,793,939 A | 12/1988 | Mori |
| 4,806,166 A | 2/1989 | Schilling |
| 4,818,117 A | 4/1989 | Krambrock |
| 4,818,783 A | 4/1989 | Shioji |
| 4,824,559 A | 4/1989 | Gilmore |
| 4,824,653 A | 4/1989 | Severinghaus, Jr. |
| 4,839,404 A | 6/1989 | Chang |
| 4,844,364 A | 7/1989 | Rossouw |
| 4,844,365 A | 7/1989 | Rossouw |
| 4,861,672 A | 8/1989 | Miyabayashi |
| 4,877,192 A | 10/1989 | Rossouw |
| 4,895,754 A | 1/1990 | Graham |
| 4,900,589 A | 2/1990 | Montgomery |
| 4,909,837 A | 3/1990 | Hansen |
| 4,923,131 A | 5/1990 | Rossouw |
| 4,933,384 A | 6/1990 | Wolfe |
| 4,940,740 A | 7/1990 | Folda |
| 4,971,615 A | 11/1990 | Manz |
| 4,975,476 A | 12/1990 | Wolfe |
| 4,985,509 A | 1/1991 | Matuura |
| 4,990,190 A | 2/1991 | Myers |
| 4,996,267 A | 2/1991 | Gerth |
| 5,007,987 A | 4/1991 | Block |
| 5,017,234 A | 5/1991 | Gartner |

| | | | | | |
|---|---|---|---|---|---|
| 5,019,610 A | 5/1991 | Sitz | 5,747,615 A | 5/1998 | Repecka |
| 5,034,498 A | 7/1991 | Himmelblau | 5,751,484 A | 5/1998 | Goodman |
| 5,039,787 A | 8/1991 | Tanaka | 5,755,865 A | 5/1998 | Lukens |
| 5,041,252 A | 8/1991 | Fujii | 5,766,333 A | 6/1998 | Lukens |
| 5,041,473 A | 8/1991 | Gau | 5,776,541 A | 7/1998 | Belt |
| 5,064,571 A | 11/1991 | Speranza | 5,782,539 A | 7/1998 | Peterson |
| 5,079,037 A | 1/1992 | Morrison | 5,786,436 A | 7/1998 | Fischer |
| 5,084,103 A | 1/1992 | Myers | 5,788,727 A | 8/1998 | Barthelmess |
| 5,094,532 A | 3/1992 | Trainer | 5,795,622 A | 8/1998 | Belt |
| 5,127,963 A | 7/1992 | Hartup | 5,806,908 A | 9/1998 | Kim |
| 5,164,787 A | 11/1992 | Igushi | 5,810,427 A | 9/1998 | Hartmann |
| 5,174,581 A | 12/1992 | Goodson | 5,859,306 A | 1/1999 | Stanforth |
| 5,185,641 A | 2/1993 | Igushi | 5,860,908 A | 1/1999 | Forrester |
| 5,193,936 A | 3/1993 | Pal et al. | 5,877,393 A | 3/1999 | Webster |
| 5,196,620 A | 3/1993 | Gustin | 5,882,377 A | 3/1999 | Aida |
| 5,207,949 A | 5/1993 | Niino | 5,897,685 A | 4/1999 | Goozner |
| 5,207,964 A | 5/1993 | Mauro | 5,898,093 A | 4/1999 | Vos |
| 5,211,895 A | 5/1993 | Jacklich, Sr. | 5,908,502 A | 6/1999 | Cangiano |
| 5,217,530 A | 6/1993 | Grzybowski | 5,913,972 A | 6/1999 | Kanou |
| 5,228,895 A | 7/1993 | Kelly | 5,916,947 A | 6/1999 | Morris |
| 5,240,760 A | 8/1993 | George | 5,932,502 A | 8/1999 | Longobardo |
| 5,244,481 A | 9/1993 | Nied | 5,943,231 A | 8/1999 | Thomas |
| 5,245,114 A | 9/1993 | Forrester | 5,961,710 A | 10/1999 | Linde |
| 5,252,003 A | 10/1993 | McGahan | 5,968,248 A | 10/1999 | Shibasaki |
| 5,264,318 A | 11/1993 | Yabe | 5,993,530 A | 11/1999 | Tanaka |
| 5,278,982 A | 1/1994 | Daniels | 6,001,185 A | 12/1999 | Huff |
| 5,286,291 A | 2/1994 | Bernhardt | 6,007,590 A | 12/1999 | Sanders, Jr. |
| 5,316,313 A | 5/1994 | Moore | 6,029,395 A | 2/2000 | Morgan |
| 5,326,827 A | 7/1994 | Aoki | 6,053,967 A | 4/2000 | Heilmann |
| 5,337,824 A | 8/1994 | Cowan | 6,063,447 A | 5/2000 | Morand |
| 5,341,939 A | 8/1994 | Aitchison | 6,083,289 A | 7/2000 | Ono |
| 5,349,003 A | 9/1994 | Kato | 6,093,494 A | 7/2000 | Schulz |
| 5,352,275 A | 10/1994 | Nath | 6,095,082 A | 8/2000 | Belt |
| 5,356,664 A | 10/1994 | Narayan | 6,096,835 A | 8/2000 | Vandevoorde |
| 5,360,860 A | 11/1994 | Itoh | 6,109,913 A | 8/2000 | Young |
| 5,374,405 A | 12/1994 | Firnberg | 6,156,289 A | 12/2000 | Chopra |
| 5,375,779 A | 12/1994 | Ephraim | 6,183,727 B1 | 2/2001 | Gust, Jr. |
| 5,380,552 A | 1/1995 | George | 6,191,853 B1 | 2/2001 | Yamaguchi |
| 5,380,837 A | 1/1995 | Nakada | 6,197,879 B1 | 3/2001 | Fischer |
| 5,382,449 A | 1/1995 | Hedges | 6,245,723 B1 | 6/2001 | Sigg |
| 5,389,353 A | 2/1995 | Glaeser | 6,252,658 B1 | 6/2001 | Togawa |
| 5,397,478 A | 3/1995 | Pal | 6,258,456 B1 | 7/2001 | Meyer |
| 5,405,648 A | 4/1995 | Hermann | 6,281,972 B1 | 8/2001 | Ebara |
| 5,411,803 A | 5/1995 | George | 6,290,772 B1 | 9/2001 | Cheung |
| 5,421,906 A | 6/1995 | Borah | 6,291,067 B1 | 9/2001 | Taoda |
| 5,430,223 A | 7/1995 | Bauer | 6,294,247 B1 | 9/2001 | Watanabe |
| 5,430,234 A | 7/1995 | Willis | 6,306,796 B1 | 10/2001 | Suzue |
| 5,431,939 A | 7/1995 | Cox | 6,351,676 B1 | 2/2002 | Thomas |
| 5,439,056 A | 8/1995 | Cowan | 6,358,305 B1 | 3/2002 | Joedicke |
| 5,443,632 A | 8/1995 | Schilling | 6,358,319 B1 | 3/2002 | Huykman |
| 5,460,741 A | 10/1995 | Hata | 6,362,121 B1 | 3/2002 | Chopin |
| 5,511,899 A | 4/1996 | Pavelek, II | 6,368,668 B1 | 4/2002 | Kobayashi |
| 5,512,521 A | 4/1996 | Fu | 6,369,399 B1 | 4/2002 | Smirnov |
| 5,516,458 A | 5/1996 | Lelental | 6,383,398 B2 | 5/2002 | Amer |
| 5,516,573 A | 5/1996 | George | 6,383,980 B1 | 5/2002 | Hagihara |
| 5,541,096 A | 7/1996 | Nomura | 6,403,687 B1 | 6/2002 | Schulz |
| 5,541,831 A | 7/1996 | Thomas | 6,454,951 B1 | 9/2002 | Jori |
| 5,547,596 A | 8/1996 | Omiya | 6,465,058 B2 | 10/2002 | Huykman |
| 5,558,702 A | 9/1996 | Chatterjee | 6,465,107 B1 * | 10/2002 | Kelly ......................... 428/447 |
| 5,566,576 A | 10/1996 | Sher | 6,482,780 B2 | 11/2002 | Yokouchi |
| 5,573,331 A | 11/1996 | Lin | 6,503,740 B1 | 1/2003 | Alther |
| 5,578,771 A | 11/1996 | Karhu | 6,547,948 B1 | 4/2003 | Soppe |
| 5,651,550 A | 7/1997 | LaVorgna | 6,555,607 B1 | 4/2003 | Kanda |
| 5,658,886 A | 8/1997 | Chizhov | 6,573,340 B1 | 6/2003 | Khemani |
| 5,660,498 A | 8/1997 | Freeman | 6,590,133 B2 | 7/2003 | Stanforth |
| 5,667,577 A | 9/1997 | Chatterjee | 6,607,781 B2 | 8/2003 | Joedicke |
| 5,667,729 A | 9/1997 | Shimbori | 6,608,121 B2 | 8/2003 | Isozaki |
| 5,678,235 A | 10/1997 | Crowe | 6,613,388 B1 | 9/2003 | Kashiwabara |
| 5,681,361 A | 10/1997 | Sanders, Jr. | 6,616,451 B1 | 9/2003 | Rizolu |
| 5,682,235 A | 10/1997 | Igushi | 6,629,792 B1 | 10/2003 | Geddes |
| 5,686,178 A | 11/1997 | Stevens | 6,637,354 B2 | 10/2003 | Ramme |
| 5,709,433 A | 1/1998 | Christopher | 6,654,627 B2 | 11/2003 | Petrenko |
| 5,746,830 A | 5/1998 | Burton | 6,664,479 B2 | 12/2003 | Tanabe |

| | | | | | | |
|---|---|---|---|---|---|---|
| 6,683,023 B2 | 1/2004 | Ito | 6,835,688 B2 | 12/2004 | Morikawa | |
| 6,688,811 B2 | 2/2004 | Forrester | 6,864,979 B2 | 3/2005 | Yamaguchi | |
| 6,692,544 B1 | 2/2004 | Grillenzoni | 6,875,341 B1 | 4/2005 | Bunger | |
| 6,700,066 B1 | 3/2004 | Kuo | 6,882,517 B2 | 4/2005 | Tano | |
| 6,717,363 B2 | 4/2004 | Foust | 6,890,872 B2 | 5/2005 | Bond | |
| 6,720,066 B2 | 4/2004 | Talpaert | 6,916,505 B2 * | 7/2005 | Raymond et al. | 427/403 |
| 6,720,367 B2 | 4/2004 | Taniguchi | 7,037,956 B2 | 5/2006 | Liu | |
| 6,722,271 B1 | 4/2004 | Geddes | 7,060,658 B2 | 6/2006 | Joedicke | |
| 6,736,991 B1 | 5/2004 | Cohen | 7,098,258 B2 | 8/2006 | Ideno | |
| 6,781,302 B2 | 8/2004 | Sigai | 2002/0160151 A1 | 10/2002 | Pinault | |
| 6,786,963 B2 | 9/2004 | Matherly | 2004/0110639 A1 * | 6/2004 | Joedicke | 504/151 |
| 6,794,065 B1 | 9/2004 | Morikawa | 2005/0029496 A1 | 2/2005 | Schwark | |
| 6,796,733 B2 | 9/2004 | Geddes | 2007/0082126 A1 | 4/2007 | Aschenbeck | |
| 6,803,016 B2 | 10/2004 | Edlinger | | | | |
| 6,809,128 B2 | 10/2004 | Ohta | | | | |

\* cited by examiner

MINERAL COMPOSITION

CROSS-REFERENCE TO RELATED PATENT APPLICATION

This patent application is a continuation-in-part of applicant's copending patent application Ser. No. 11/638,618, filed on Dec. 13, 2006, which in turn was a continuation-in-part of patent application Ser. No. 11/266,833, filed on Nov. 4, 2005. The entire disclosure of each of such copending patent applications is hereby incorporated by reference into this specification.

This patent application also claims priority based upon International Patent Application PCT/US2006/022389, that was published as International Publication No. WO 2006/13384 A2 on Dec. 14, 2006.

FIELD OF THE INVENTION

A mineral composition comprised of at least 50 weight percent of calcium carbonate, from about 0.1 to about 1 weight percent of a pigmented material, and from about 0.1 to about 1.0 weight percent of a means for inhibiting the growth of an organism selected, e.g., from the group consisting of algae, bacteria, and mixtures thereof; the composition has superior granule adhesion properties as measured by ASTM Standard Test D 4977-03.

BACKGROUND OF THE INVENTION

An International Search Report for International patent application PCT/US06/22389 was issued on Jan. 29, 2007 The references found included U.S. Pat. No. 4,329,179 of Kutta; published United States patent application 2002/0160151 A1 of Pinault et al., and an article entitled "A Review of Methods for the Manufacture of Residential Roofing Materials (Akibari et al.), dated June 2003. These were reported to be "A" documents, i.e., documents" . . . defining the general state of the art which is not considered to be of particular relevance."

Roofing shingles are comprised of a headlap portion and a butt portion; granules are often used in both of such portions. Reference may be had, e.g., to U.S. Pat. Nos. 3,921,358 (a composite asphalt-impregnated felt roofing shingle comprising a rectangular sheet having a headlap portion and a butt portion), 4,717,614 (a shingle whose headlap portion is coated with a layer of asphaltic material), 4,900,589 (a process for applying granules to a moving sheet having a headlap area and a butt area for making a shingle roofing product), 6,358,305 (a process of preparing a darkened headlap for a roofing shingle), and the like. The entire disclosure of each of these United States patents is hereby incorporated by reference into this specification.

Many abrasive materials, and many roofing granules (such as headlap granules and prime granules), are made from slag. Processes for making granules from slag are well known. Reference may be had, e.g., to U.S. Pat. Nos. 3,615,329, 4,358,415 (method for producing granules from molten metallurgical slags), 4,374,645 (process for granulation of slag), 4,758,260 (process and device for producing granulated slag sand from blast furnace slag), 4,909,837 (process for granulating molten slag), 6,803,016 (device for atomizing and granulating liquid slags), and the like.

Roofing granules made from coal slag are also well known. Coal slag, and its properties have been widely described in the patent literature. Reference may be had, e.g., to U.S. Pat. Nos. 3,995,079 (artificial turf-like product), 4,174,974 (process for converting coal slag into Portland cement), 4,576,638 (process for the production of ferromanganese), 4,629,506 (process for the production of ferrochromium), 4,971,615 (method and means for producing mineral wool), 5,211,895 (molding process for forming a concrete block) 5,337,824 (coal slag universal fluid), 5,405,648 (coating particulate material with a polymer film), 5,439,056 (coal slag solidification of drilling fluid), 5,681,361 (method of making an abrasive article), 6,001,185 (method for treatment of heavy metal contamination), 6,007,590 (method of making a foraminous abrasive article), 6,109,913 (method for disposing of waste dust), and the like.

Coal slag is also often referred to as "Cyclone Boiler Slag," "Cyclone Bottom Ash," "Bottom Ash," "Slag Residue," "Black Jack," etc. Granules made from such coal slag often contain substantial amounts of toxic metals, such as, e.g., arsenic, barium, cadmium, chromium, lead, mercury, selenium, and silver. The concentrations of these metals in a particular matrix may be measured by well known methods such as, e.g., the "Toxicity Characteristic Leaching Procedure" (TCLP), which is described, e.g., in EPA method SW 846-1311.

Heavy metals (such as arsenic, barium, cadmium, chromium, lead, mercury, selenium, and silver) are found to contaminate ground water and, when consumed via drinking water and certain injected foods, they accumulate over time in the human body tissue.

Essential metals are required by all organisms in small quantities in order to accomplish specific catalytic functions. However, at levels exceeding these requirements, both essential and non-essential metals can disturb metabolism by binding non-specifically to biomolecules and by inflicting oxidative damage due to their ability to catalyze redox reactions. This can result in the deactivation of essential enzymatic reactions, damage to cellular structures (especially membranes), and DNA modification (mutagenesis). In humans, exposure to high levels of metals can cause acute toxicity symptoms, while long-term exposure to lower levels can trigger allergies and even cancers. In all organisms, uptake, localization, cytoplasmic concentration, and targeting of micronutrient metals must be tightly controlled in order to meet nutritional needs while avoiding damage. Any non-essential metals that enter organisms by virtue of their chemical similarity to nutrient ions must be detoxified and/or excreted.

Metals tend to accumulate in animals and plants. They enter aquatic organisms through body and respiratory surfaces, and by ingestion of particulate matter and water. Toxicity manifests as impairment of metabolic function, with possible changes to the distribution and abundance of populations. Sublethal effects may include changes in morphology, physiology, biochemistry, behavior and reproduction. Massive fish kills can occur when aluminum and iron are mobilized with drainage from acid sulfate soils. The extent of metal uptake, toxicity and bioaccumulation varies depending on the organism, and can be modified by temperature, pH, turbidity, dissolved oxygen and the concentrations of other metals in solution. Accumulation of metals by aquatic organisms (e.g., bivalves and crabs can be a useful indicator of the presence of metals in biologically available forms. If metal levels in organisms are too high for human consumption, shell-fishing waters are closed.

Coal slag and roofing granules made therefrom, are believed to contain one or more of the aforementioned heavy metals. It is not known to what extent, if any, coal slag particles that are disposed within a biological organism degrade and release either heavy metals and/or other contaminants to the biological organism.

It is known, however, that many products derived from coal, such as coal tar, contain substantial amounts of polycyclic aromatic hydrocarbons (PAH). As is disclosed in an article by D. James Fitzgerald et al., "Application of Benzo(a)pyrene and Coal Tar Tumor Dose—Response Data to a Modified Benchmark Dose Method of Guideline Development," Environmental Health Perspectives, Volume 112, Number 14, October, 2004, pages 1341-1346, "Polycyclic aromatic hydrocarbons . . . are found at a variety of contaminated sites throughout the world from industries such as coal gasification, coke production . . . and cresoste and asphalt production. Some PAHs, for example the well-studied benzo(a)pyrene . . . , are mutagenic and carcinogenic in experimental animals and probably in humans also . . . ." (See page 1341.)

It is an object of this invention to provide granular materials that can function as roofing granules and that contain less than about 100 parts per million of leachable heavy metals via EPA method SW 846-1311 but that have good adhesion properties when incorporated into a roofing shingle.

It is another object of this invention to provide granular materials that can function well as roofing granules but that do not contain any polycyclic aromatic hydrocarbons and have good adhesion properties when incorporated into a roofing shingle.

It is yet another object of this invention to provide granular materials that, in response to electromagnetic radiation, provides a means for inhibiting the growth of undesirable organisms such as, e.g., algae, bacteria, and mixtures thereof.

SUMMARY OF THE INVENTION

In accordance with this invention, there is provided a mineral composition comprised of at least about 90 weight percent of roofing granules, at least about 50 weight percent of calcium carbonate with a hardgrove grindability index of less than about 70, from about 0.1 to about 1.0 weight percent of a pigmented material, A mineral composition comprised of at least 50 weight percent of calcium carbonate, from about 0.1 to about 1 weight percent of a pigmented material, from about 0.1 to about 1.0 weight percent of a composition for inhibiting the growth of an organism selected from the group consisting of algae, bacteria, and mixtures thereof, less than about 100 parts per million of a metal selected from the group consisting from the group consisting of arsenic, barium, cadmium, chromium, lead, mercury, selenium, and silver, and less than about 100 parts per million of a polycyclic aromatic hydrocarbon. The mineral composition, when tested in accordance with ASTM Standard Test D 4977-03, loses less than 5 grams of material.

BRIEF DESCRIPTION OF THE DRAWINGS

The invention will be described by reference to the following drawings, in which like numerals refer to like elements, and wherein.

DESCRIPTION OF THE PREFERRED EMBODIMENTS

Figure 1:
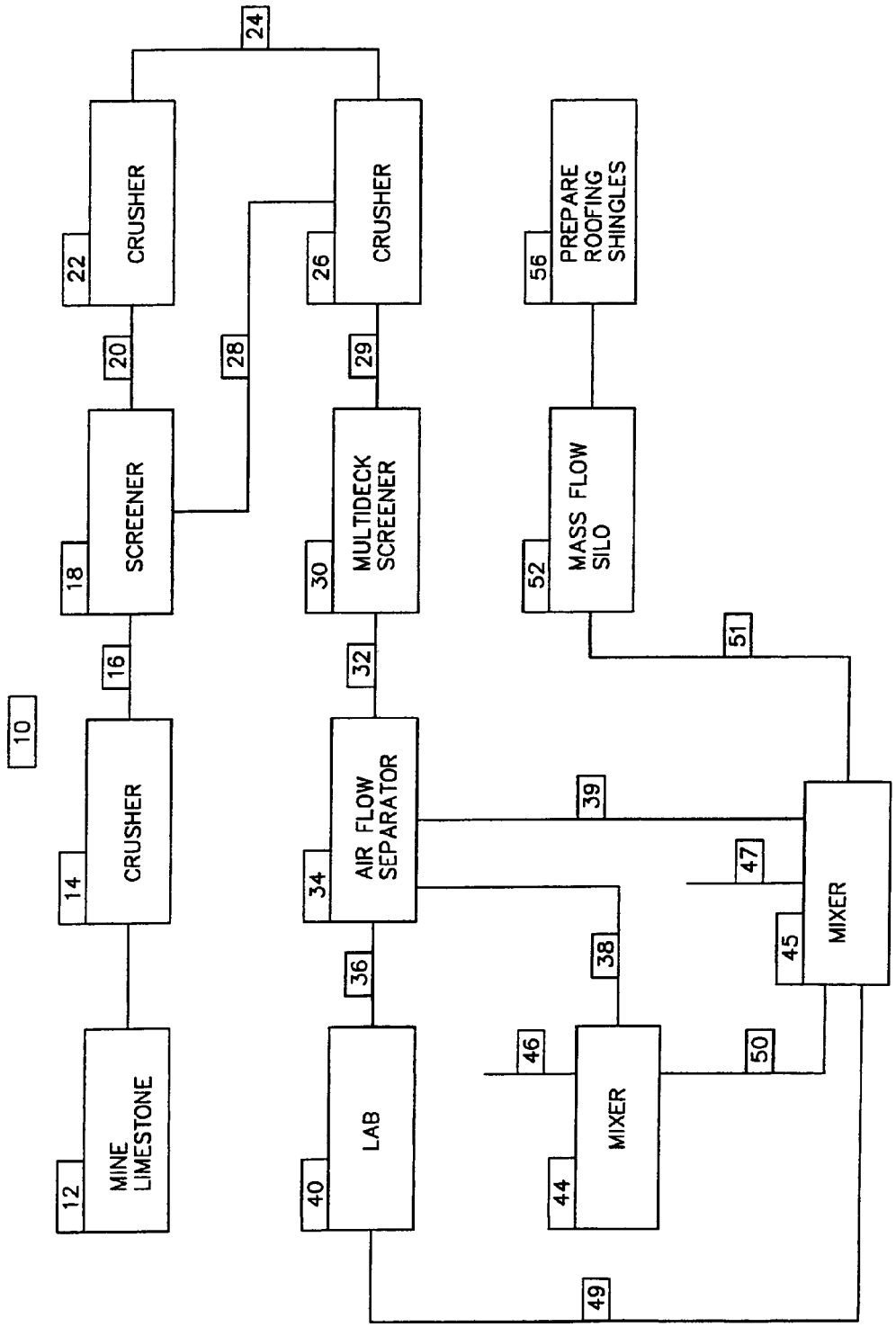
FIG. 1 is a flow diagram of one preferred process of the invention.

Roofing granules are well known to those skilled in the art. Reference may be had, e.g., to U.S. Pat. Nos. 3,884,706 (algicidal roofing granules), 4,092,441 (roofing granule treatment by coating with a metallic algicide), 4,359,505 (light colored roofing granules), 5,380,552 (method of improving adhesion between roofing granules and asphalt-based roofing materials), 6,156,289 (iron based roofing granules and method of coloring the same), 6,607,781 (roofing granules with a decorative metal appearance), 7,060,658 (roofing granules), and the like. The entire disclosure of each of these United States patents is hereby incorporated by reference into this specification.

Roofing granules made from coal slag have excellent adhesion properties. However, some have expressed concerns about the safety of coal slag (in general) and of roofing granules made from coal slag. It would be desirable to be able to make roofing granules with good adhesion properties from a more "environmentally friendly" material than coal slag.

Limestone is a substantially more "environmentally friendly" material than coal slag. Thus, e.g., limestone is often fed to chickens as a feed supplement. However, the adhesion properties of limestone granules are often not deemed to be adequate for use in roofing shingles.

Adhesion Properties and Adhesion Testing of Roofing Granules

The adhesion properties of roofing granules is extensively discussed in U.S. Pat. No. 5,380,552 ("Method of improving adhesion between roofing granules and asphalt-based material), the entire disclosure of which is hereby incorporated by reference into this specification.

At lines 37-48 of U.S. Pat. No. 5,380,552, it is disclosed that "The exterior, outer, or exposed surface of asphalt roofing systems and products is generally provided with a covering of granular material or roofing granules embedded within the coating asphalt. The granular material generally protects the underlying asphalt coating from damage due to exposure to light, in particular ultraviolet (UV) light. That is, the granules reflect light and protect the asphalt from deterioration by photodegradation. In addition, such granular material improves fire resistance and weathering characteristics. Further, colors or mixtures of colors of granular material may be selected for aesthetics."

The adherence of the roofing granules to the roofing product is discussed at lines 56-63 of column 1 of U.S. Pat. No. 5,380,552, wherein it is disclosed that: "Good adherence of the roofing granules to the roofing product is beneficial. Loss of granules reduces the life of the roof, since it is associated with acceleration of photodegradation of the asphalt. In addition, the aesthetics of the roofing system may be compromised if granules are lost. Further, reduction of granule loss during installation improves safety conditions on the roof."

Granule loss due to abrasion is discussed at the last paragraph of column 1 of U.S. Pat. No. 5,380,552, wherein it is disclosed that, "Granule loss can also occur due to physical abrasion of the granular surface. This may occur any time a person walks on an installed roof for maintenance, during installation of the roofing surface or by such environmental conditions as tree branches rubbing on the granular surface and the physical contact of rain or hail with the roofing surface."

The benefits of reducing such granule loss are discussed at lines 34-37 of column 4 of U.S. Pat. No. 5,380,552, wherein it is disclosed that, "Improved granule retention increases the useful life of the roofing system by inhibiting exposure of the asphalt layer to ultraviolet light and thus inhibiting photodegradation of the coating asphalt."

At lines 53 (of column 4) to 10 (of column 5), the substrate used in making roofing shingles is discussed. It is disclosed that, "A variety of materials may be utilized as the substrate for the roofing materials. In general, preferred materials comprise a non-woven matting of either fiberglass or cellulose fibers. Fiberglass matting is used most widely in the asphalt roofing products industry and is a typical and preferred substrate for use with methods and in products according to the present invention. Cellulose matting, sometimes referred to as organic matting or rag felt may also be utilized. Fiberglass matting is commercially available from Owens-Corning Fiberglass Corporation, Toledo, Ohio and Manville Roofing Systems, Denver, Colo. These commercially-available substrates are utilized in preferred embodiments of the present invention. It is recognized that any fiberglass mat with similar physical properties could be incorporated into the process of the present invention with satisfactory results. Generally, the fiberglass matting is manufactured from a silicate glass fiber blown in a non-woven pattern in streams of about 30-200 micrometers in diameter with the resultant mat approximately 1-5 millimeters in thickness. Cellulose felt (dry felt) is typically made from various combinations of rag, wood and other cellulose fibers or cellulose-containing fibers blended in appropriate proportions to provide the desirable strength, absorption capacity and flexibility."

At lines 13-39 of column 5 of U.S. Pat. No. 5,380,552, the asphalt used in making roofing flux is disclosed. In this section of such patent, it is stated that: "Roofing asphalt, sometimes termed "asphalt flux", is a petroleum based fluid comprising a mixture of bituminous materials. In the manufacture of roofing it is generally desirable to soak the absorbent felt or fiberglass mat until it is impregnated or saturated to the greatest possible extent with a "saturant" asphalt, thus the asphalt should be appropriate for this purpose. Saturant asphalt is high in oily constituents which provide waterproofing and other preservatives. Substrates saturated with saturant asphalt are generally sealed on both sides by application of a hard or more viscous "coating asphalt" which itself is protected by the covering of mineral granules. In the case of fiberglass mat based asphalt roofing products, it is well understood that the coating asphalt can be applied directly to the unsaturated fiberglass mat. The asphalts used for saturant asphalt and the coating asphalt are prepared by processing the asphalt flux in such a way as to modify the temperature at which it will soften. The softening point of saturant asphalt varies from about 37° C. to about 72° C., whereas the softening point of desirable coating asphalt runs as high as about 127° C. The softening temperature may be modified for application to roof systems in varying climates. In general, conventional, commercially available, asphalt systems may be utilized in applications of the present invention."

A conventional means of making roofing shingles is discussed at columns 7-9 of U.S. Pat. No. 5,380,552. In the paragraph beginning at lines 46 of column 7 of such patent, it is disclosed that, "A schematic generally illustrating preparation of roofing shingles according to the present invention is illustrated in FIG. 1. Except for addition of adhesives as described, and modifications to accommodate addition of adhesives as described, the system in FIG. 1 is generally as presented in U.S. Pat. No. 4,352,837 Kopenhaver), incorporated herein by reference. In operation, a roll of dry felt or bonded fiberglass mat 12, (the substrate) in sheet form, is installed on a feed roll 13 and unwound onto a dry looper 14. The dry looper 14 acts as a reservoir of mat material that can be drawn upon during the manufacturing operation to inhibit stoppages which might otherwise occur when new or additional rolls are fed into the system. Dry felt, or mat 12, is subjected to a hot asphalt saturating process, indicated generally at 15, after it passes through dry looper 14. The purpose of the asphalt saturating process 15 is to eliminate moisture and to fill the intervening spaces of the fibers of the substrate 12 as completely as possible. The saturating process is conducted in a saturation tank 16 in which saturating asphalt is contained. Sufficient heat is added to maintain the saturant asphalt in saturation tank 16 as a flowable liquid, typically at application temperatures of at least about 70° C."

In the paragraph beginning at line 3 of column 8 of U.S. Pat. No. 5,380,552, it is disclosed that: "Following saturation tank 16, the saturated web 17 is passed through wet looper 18 whereat it is cooled and shrunk, permitting excess asphalt material to be further drawn into the substrate. The mat 12, after saturation with saturating asphalt in tank 16, is next passed through looper 18 and is then directed into coating area 20, for uniform coating with a coating asphalt, to the top and bottom of the mat. Coating area 20 contains a material reservoir 22 and an applicator with a distributor nozzle 23, which are operated to apply the asphalt coating material to the top surface of the mat. Excess coating material flows over the sides of the substrate and into a pan (not shown) from which it is picked up by adjustable rollers 25 for application to the bottom of the web, in a uniform layer. If, the mat 12 comprises a fiberglass mat, it is well accepted in the industry that the coating asphalt can be directly applied to an unsaturated fiberglass mat, although it may be saturated first. Thus, the above-described process can be modified by feeding the fiberglass mat 12 directly from dry looper 14 to the coating area 20. At station 30, an adhesive reservoir 31 and applicator with distributor nozzle 32 are shown. The hot-melt adhesive is contained within adhesive reservoir 31 and is distributed to the upper surface of asphalt-coated web 33 by distributor nozzle 32. The adhesive may be applied in a variety of patterns and manners. In general, satisfactory results are obtained if the adhesive is applied in thin streams on the order of about 100-200 micrometers in diameter, for example with a blown-fiber adhesive spray gun such as that manufactured by PAM Fastening Technology, Model PAM 500KS. The thin streams may be applied in a random pattern or in other patterns. In general, for some improvement all that is required is that an effective amount of adhesive be applied to the asphalt-coated web 33 upper surface to which granular material is eventually applied. By the term "effective amount", in this context, it is meant that an amount of adhesive is applied such that with respect to loss of granular material due to moisture attack or deterioration, the resulting product is improved. In addition, in many applications such an amount of adhesive will also improve dry adhesion. Hereinbelow, a 'wet rub test' and a 'dry rub test' are described, by which improvement can be evaluated." The dry rub test is conducted in accordance with ASTM Standard Test D 4977, and this standard test is also used in the present invention to determine the grams of granules lost.

In the paragraph beginning at line 49 of column 8 of U.S. Pat. No. 5,380,552, it is disclosed that: "Preferably the adhesive is distributed in thin streams of about 100-200 micrometers diameter until at least about 25% and more preferably 50-75% of the upper surface of asphalt-coated web 33 is covered thereby. Preferably, the adhesive is applied while the coating asphalt is still hot, i.e. on the order of at least 170° C. (340° F.). Still referring to FIG. 1, roofing granules are contained within hopper or blender 24. They are applied to the upper surface of adhesive-coated web 43 by gravity feed through granule distributor 42. Excess granules may be picked up by a mechanism generally indicated at spill area 46. In addition, the underside 44 of web 43 may be coated with talc, mica or other suitable materials which are applied by a distributor 48. In order to obtain proper adhesion of the granules, the sheet granules are subject to controlled pressure by compression rollers or drums 51 which force the granules into the asphaltic coating material (and adhesive) a predetermined depth. Cooling may be added to these drums or rollers to cool the hot asphalt as the granules are pressed or embedded therein."

In the paragraph beginning at line 3 of column 9 of U.S. Pat. No. 5,380,552, it is disclosed that: "The web with granules embedded therein, 52, then travels through tension roller area 53 which assists in feeding the web material through the previously-disclosed process. The web material 52, with the granules embedded therein, is then fed to a finished or cooling looper 50. The primary function of this looper is to cool the sheet down to a point where it can be cut and packed without danger to the material. Subsequent to the cooling looper 50, the sheet may be fed to a roll roofing winder 54. Here the sheet is wound on a mandrel which measures the length of the material as it turns. When sufficient material has accumulated it is cut off, removed from the mandrel and passed on for wrapping. Alternatively, the sheet leaving the cooling looper 50 may be fed to a shingle cutter 56. It will be understood that the finished sheet or web may be cut to desired shapes or sizes and it may be modified, for example, by the addition of liners, application adhesives, or other modifications. The cut shapes or sizes are transferred to a stacking/packing area 58. The type of processing described above is well-known in the manufacturing of shingles or other roof materials, for example, as described in U.S. Pat. No. 4,352,837, which is incorporated herein by reference."

A "Dry Rub Test" for determining the extent of adherence of the roofing granules is described at lines 12-46 of column 10 of U.S. Pat. No. 5,380,552. ASTM standard test D 4977-89 was used for the "Dry Rub Test" used in U.S. Pat. No. 5,380, 837. ASTM test D 4977-03 is also used for the "Dry Rub Test" described in this specification.

As is disclosed at lines 12-46 of column 10 of U.S. Pat. No. 5,380,552, "The dry rub test is a standard test method for the determination of granular adhesion to mineral-surfaced roofing under conditions of abrasion. The procedure is described in ASTM standard D 4977-89, incorporated herein by reference. Dry rub tests conducted to evaluate granular adhesion in products according to the present invention, were conducted in compliance with this standard. In general, a brush with 22 holes, each containing bristles made of 0.012 inch diameter tempered steel wire (40 wires per hole, set with epoxy) was used to abrade the granular surface of a specimen of mineral-surfaced roofing. The adhesion is assessed by weighing the amounts of granules that are displaced and become loose as a result of the abrasion test. The testing apparatus is a machine designed to cycle a test brush back and forth (horizontally) across a specimen at a rate of 50 cycles in a period of about 60-70 seconds while the brush assembly rests on the specimen with a downward mass of 5 pounds±¼ ounce with a stroke link of 6±¼ inch. The testing machine used is available commercially, as the 3M Granule Embedding Test Machine and Abrasion Test Brushes, Minnesota Mining & Manufacturing, Inc., St. Paul, Minn. A minimum of two 2-inch by 9-inch specimens were utilized for each test, and any loose granules were removed from the specimen with gentle tapping. Each specimen was then weighed and the mass was recorded. The specimen was then clamped to the test machine and the brush was placed in contact with the specimen (with activation of the machine so that the specimen was abraded 50 complete cycles, the brush traveling parallel to the long axis of the specimen). The specimen was then removed and weighed; the loss in mass then being calculated."

It is preferred to determine the adhesion properties of the roofing granules by a procedure in which the granules are incorporated into a roofing shingle and the shingle is tested in accordance with ASTM 4977-03.

The test samples used to determine the adhesive characteristics of the coated granule particles are constructed using a petroleum based roofing asphalt which as been oxidized by blowing with air at a temperature of approximately 500° Fahrenheit, with a final Ring & Ball Softening Point of between 195° F. and 215° F. as determined by ASTM D 36, and a Needle Penetration of between 17 dmm and 23 dmm @ 77° F., as determined by ASTM D 5, this material typically referred to in the trade as Asphalt Shingle Coating.

A commercially available bonded non-woven glass roofing fabric with a dry weight of approximately 92-95 grams/m$^3$, consisting of sized individual "E" Glass filaments of 15.25-16.5 microns in diameter ("M" fiber) and from 0.75-1.25 inches in length, which are randomly oriented and bonded with a modified urea-formaldehyde resin binder, which has been applied to a level of 20% (dry weight), is coated on each side and saturated with a roofing asphalt compound consisting of Asphalt Shingle Coating containing at least 65% of a mineral filler such as limestone or stone dust, such compound typically referred to in the trade as Filled Asphalt Coating. The asphalt coated sheet is allowed to cool to room temperature.

The asphalt coated sheet is conditioned, preferably in an oven at 150 degrees Fahrenheit for 30 minutes. After conditioning, samples of granule particles produced in the process depicted in FIG. 1 are applied to the top surface of the warm sheet by gravity feed, and the granule particles are roll pressed into the sheet. The finished sheet is allowed to cool to room temperature and is then cut into 2 inch by 9 inch sample specimens for further testing under ASTM D 4977-03. All loose granule particles are removed from the samples by gentle tapping of the specimen At least two sample specimens are cut for each trial, with the long dimension of the specimen in the machine direction. Specimens are conditioned at room temperature of 23° C. plus or minus 2° C. (73.4° F. plus or minus 3.6° F.) for at least 30 minutes before testing. Granule abrasion tests are done using a Granule Test Apparatus as described in ASTM Procedure D 4977-03. All loose granules are removed from the specimens by gentle tapping of the sample. Each specimen is weighed to the nearest 0.01 grams and a record is made of the initial weight of the specimen. The specimen is centered in the sample holder of the Test Apparatus with the mineral surface facing up and the long axis of the specimen aligned with the brush stroke of the Test Apparatus. The Test Apparatus is activated such that the specimen is abraded 50 complete cycles, each cycle consisting of a forward stroke and a back-stroke, with the brush travel remaining parallel to the long axis of the specimen. The specimen is removed from the sample holder and any loose granules are removed from the sheet by gently tapping the sample. The specimen is weighed to the nearest 0.01 grams and a record is made of the final weight of the specimen. The difference in weights for multiple samples of the same specimen are calculated and averaged to determine the average granule loss by abrasion.

In the remainder of this specification, applicants will discuss their process for preparing the roofing granules of their invention with good adherence properties, and, in certain embodiments, with specified translucency and/or color properties.

Preparation of Calcium Carbonate Containing Roofing Granules

In this portion of the specification, applicants will discuss how they prepare their preferred calcium-carbonate containing roofing granules.

FIG. 1 is a flow diagram of a preferred process 10 for preparing some preferred limestone granules of this invention. In step 12 of this process, the limestone is mined by conventional means. The limestone so mined preferably contains at least about 50 weight percent of calcium carbonate.

Limestone, processes for mining it, processes for treating it, methods of using it, and compositions containing it are well known to those skilled in the art. Reference may be had, e.g., to U.S. Pat. Nos. 3,601,376 (process for preheating limestone), 3,617,560 (limestone neutralization of dilute acid waste waters), 3,722,867 (method of calcining limestone), 3,900,434 (wallboard tape joint composition comprised of limestone), 4,015,973 (limestone-expanding clay granules), 4,026,7632 (use of ground limestone as a filler in paper), 4,231,884 (water retardant insulation composition comprising treated low density granular material and finely divided limestone), 4,237,025 (product comprising lime or limestone and Graham's salt), 4,239,736 (method for increasing the brightness of limestone), 4,272,498 (process for comminuting and activating limestone by reaction with carbon dioxide), 4,316,813 (limestone-based sorbent agglomerates), 4,390,349 (method for producing fuel gas from limestone), 4,430,281 (process for palletizing limestone fines), 4,594,236 (method of manufacturing calcium carbide from limestone), 4,614,755 (protective coating composition comprising a blend of polyvinyl acetate, hydraulic cement, EVA, and limestone), 4,629,130 (process for preparing finely divided limestone), 4,671,208 (clay and limestone composition), 4,710,226 (fluidization of limestone slurries), 4,781,759 (limestone and clay traction aid) 4,824,653 (method of bleaching limestone), 5,228,895 (fertilizer and limestone product), 5,375,779 (process for grinding limestone to a predetermined particle size distribution), 5,908,502 (limestone filled Portland cements), and the like. The entire disclosure of each of these United States patents is hereby incorporated by reference into this specification.

Referring to FIG. 1, and in step 12 thereof, limestone is mined. One may, e.g., use many of the conventional techniques used for mining minerals. Reference may be had, e.g., to U.S. Pat. Nos. 3,737,704 (control blasting), 3,775,984 (mining method and method of land reclamation), 3,849,927 (mining method using control blasting), 4,189,184 (rotary drilling and extraction process), 4,198,097 (method of mining), 4,116,488 (in-situ mining method and apparatus), 4,134,619 (subterranean mining), 4,323,281 (method for surface mining), 4,425,057 (method of mining) 4,699,429 (mining machine system), 5,667,729 (apparatus and method for continuous mining), 5,709,433 (apparatus for continuous mining), 5,782,539 (wall-to-wall surface mining process), 5,810,427 (apparatus and method for continuous mining), and the like. The entire disclosure of each of these United States patents is hereby incorporated by reference into this specification.

It is preferred that the limestone so mined contain at least about 60 weight percent of calcium carbonate. In one preferred embodiment, the limestone so mined contains at least about 70 (and more preferably at least about 80) weight percent of calcium carbonate. In another embodiment, the limestone contains at least about 85 weight percent of calcium carbonate. In another preferred embodiment, the limestone so mined contains at least about 90 weight percent of calcium carbonate and, more preferably, at least about 95 weight percent of calcium carbonate.

In one preferred embodiment, the limestone so mined is biodegradable. As used in this specification, the term biodegradable refers to a substance that can be decomposed by the biochemical systems of biological organisms (refer to the means, e.g., by which chickens decompose limestone fed to them). Reference may be had, e.g., to U.S. Pat. Nos. 3,919,163 (biodegradable containers), 4,356,572 (biodegradable implant used as bone prosthesis), 5,174,581 (biodegradable clay pigeon), 5,316,313 (frangible biodegradable clay target), 5,651,550 (biodegradable edible target), 5,993,530 (biodegradable resin composition), 6,029,395 (biodegradable mulch mat), 6,573,340 (biodegradable polymer films), 6,890,872 (fibers comprising starch and biodegradable polymers), and the like. The entire disclosure of each of these United States patents is hereby incorporated by reference into this specification.

In one preferred embodiment, the limestone so mined contains less than 10 milligrams per kilogram of arsenic, less than 150 milligrams per kilogram of barium, less than 2 milligram per kilogram of cadmium, less than 10 milligrams per kilogram of chromium, less than 10 milligrams per kilogram of lead, less than 0.4 milligrams per kilogram of mercury, less than 2.0 milligram per kilogram of selenium, and less than 0.4 milligrams per kilogram of mercury. As will be apparent, 1 milligram per kilogram is equivalent to 1 part per million.

In one preferred embodiment, the limestone so mined contains less than about 100 parts per million of a leachable metal selected from the group consisting arsenic, barium, cadmium, chromium, lead, mercury, selenium, silver, and mixtures thereof. The presence, or absence, of such a leachable metal may be determined, e.g., in accordance with the "Toxicity Characteristic Leaching Procedure" ("TCLP") that is set forth in the Environmental Protection Agency (EPA) method SW 846-1311. This "TCLP" test is well known to those skilled in the art and is described in, e.g., U.S. Pat. Nos. 5,127,963 (process for detoxifying lead contaminated materials), 5,193,936 (fixation and stabilization of lead in contaminated soil and solid waste), 5,196,620 (fixation and utilization of ash residue from the incineration of municipal solid waste), 5,245,114 (immobilization of lead in bottom ash), 5,252,003 (attenuation of arsenic leaching from particulate material), 5,278,982 (fixation and stabilization of metals in contaminated materials), 5,397,478 (fixation and stabilization of chromium in contaminated materials), 5,421,906 (methods for removal of contaminants from surfaces), 5,430,223 (immobilization of lead in solid residues from reclaiming metals), 5,430,234 (process for removing phosphorous and heavy metals from phosphorous trichloride still bottoms residue), 5,678,235 (safe ceramic encapsulation of hazardous waste with specific shale material), 5,859,306 (method of treating arsenic-contaminated matter using aluminum compounds), 5,806,908 (water insoluble heavy metal stabilization process), 5,877,393 (treatment process for contaminated waste), 5,897,685 (recycling of CdTe photovoltaic waste), 5,898,093 (treatment process for contaminated waste), 6,717,363 (control of leachable mercury in fluorescent lamps by gelatin), 6,383,398 (composition and process for remediation of waste streams), 6,590,133 (reducing lead bioavailability), 6,637,354 (coal combustion products recovery process), 6,688,811 (stabilization method for lead projectile impact area), 6,781,302 (low pressure mercy vapor fluorescent lamps), and the like. The entire disclosure of each of these United States patents is hereby incorporated by reference into this specification.

By way of illustration, the TCLP test is discussed in U.S. Pat. No. 5,860,908, the entire disclosure of which is hereby incorporated by reference into this specification. This patent discloses that "The leaching of heavy metal bearing wastes and human and biological exposure to heavy metal content has long been of concern to environmental regulators and waste producers. Under the Resource Conservation and Recovery Act (RCRA), solid waste is classified by the U.S. Environmental Protection Agency (EPA) as hazardous waste if excessive amounts of heavy metals leach from the waste when tested under the Toxicity Characteristic Leaching Procedure (TCLP). EPA also regulates the land disposal of certain heavy metal bearing wastes depending on the content of the heavy metals regardless of the leaching potential. In addition, several state governments require solid wastes with elevated levels of heavy metals be disposed of as a hazardous waste. Disposal of waste at a hazardous waste landfill is typically more expensive than disposal at non-hazardous waste landfills."

Referring again to FIG. 1, it should be noted that not only does the limestone so mined contains less than 100 parts per million of a leachable metal selected from the group consisting arsenic, barium, cadmium, chromium, lead, mercury, selenium, silver, and mixtures thereof, but it also preferably contains less than 100 parts per million of a metal selected from the group consisting arsenic, barium, cadmium, chromium, lead, mercury, selenium, silver, and mixtures thereof, regardless of whether such metal is "leachable" in accordance with the TCLP test.)

There has been some concern expressed that roofing granules made from slag might contain carbon-containing residues that might be mutagenic and/or carcinogenic when incorporated into living biological organisms. Thus, e.g., the "oxidation products" from cigarette smoke have been reported to contain many different mutagen and/or carcinogens. Similarly, the "oxidation products" produced by cooking a steak over a very high flame also contain many mutagens and/or carcinogens.

It appears that many roofing granules are prepared by combusting coal. Thus, e.g., U.S. Pat. No. 6,258,456, the entire disclosure of which is hereby incorporated by reference into this specification, discusses the preparation of roofing granules from slag produced from the combustion of coal, disclosing that, "Each year many tons of materials such as slag and fly ash resulting from combustion of coal in boilers, hereinafter referred to as coal slag and coal fly ash, found in electric generating plants are produced. In the United States in 1993, for example, over 5.6 million metric tons of coal slag and 43.7 million metric tons of coal fly ash were produced as coal combustion byproducts. The greatest use of such materials is found in roofing granules and as sandblasting materials. Other uses are found in cement and concrete products, snow and ice control, and grouting materials. However, only about 55% of the coal slag and only about 22% of the coal fly ash is incorporated into useful products. The remaining amount is generally disposed of in landfills."

Referring again to FIG. 1, and in one preferred embodiment, both the limestone mined (see FIG. 1) and the coated granular material made therefrom (see FIG. 1) preferably contain less than 100 parts per million of a metal selected from the group consisting arsenic, barium, cadmium, chromium, lead, mercury, selenium, silver, and mixtures thereof.

In one preferred embodiment, the mined limestone used in the roofing granules of this invention has a hardgrove grindability index (HGI) of less than about 70 and, more preferably, less than about 68. The hardgrove grindability index is well known to those skilled in the art and is described, e.g., in the specification and the claims of U.S. Pat. Nos. 4,419,456 (method for the disposal of shot coke), 4,521,278 (method for producing needle coke), 5,007,987, 5,389,353, 5,882,377, 6,882,517, and the like. The entire disclosure of each of these United States patents is hereby incorporated by reference into this specification.

The test for determining the hardgrove grindability index is described in A.S.T.M. Standard Test D409-85" Standard Test Method for Grindability of Coal by the Hardgrove-Machine Method." This A.S.T.M. test is also described, e.g., in U.S. Pat. Nos. 4,420,445 (coal pellets production), 4,419,456, 6,083,289, 6,692,544, and the like. The entire disclosure of each of these United States patents is hereby incorporated by reference into this specification.

Referring again to FIG. 1 and in step 14 thereof, the limestone from step 12 that preferably has the required degree of hardgrove grindability is subjected to primary crushing in step 14.

In one preferred embodiment, and referring again to FIG. 1, a rotary impact crusher is used to crush the limestone. These crushers are well known and are described, e.g., in U.S. Pat. Nos. 3,608,841 (rotary impact crusher), 3,737,678 (rotary impact crusher having a continuous rotary circumference), 4,844,364 (rotary impact crusher), 4,844,365 (rotary impact crusher), 4,877,192 (rotary impact crusher main wear tip), 4,923,131 (rotary impact crusher rotor), and the like. The entire disclosure of each of these United States patents is hereby incorporated by reference into this specification.

Referring again to FIG. 1, and to step 14 thereof, in one aspect of this embodiment, the size of the limestone is reduced in step 14 to minus 4 inches, i.e., the top maximum size is less than 4 inches.

Referring again to FIG. 1, and to the preferred embodiment depicted therein, the material from crusher 14 is preferably fed via line 16 to screener 18, which separates the material so fed into various size fractions. One may use any of the screeners known to those skilled in the art. Thus, one must use a vibratory screener such as, e.g., a screener utilizing mechanical vibration with inclined screen surfaces, a screener using mechanical vibration with horizontal screen surfaces, an electromagnetic vibratory screener, and the like.

By way of further illustration, one may use one or more of the screening devices disclosed at pages 21-39 to 21-45 of Robert H. Perry et al.'s "Chemical Engineer's Handbook," Fifth Edition (McGraw-Hill Book Company, New York, N.Y., 1973. Thus, e.g., one may use Grizzly screens (see pages 21-40 to 21-41), revolving screens (see page 21-41), mechanical shaking screens (see page 21-41), vibrating screens (see page 21-41), mechanically vibrated screens (see page 21-41), electrically vibrated screens (see page 21-41), oscillating screens (see page 21-42), reciprocating screens (see page 21-42), gyratory screens (see page 21-42), gyratory riddles (see page 21-42), and the like.

In one preferred embodiment, and referring again to FIG. 1, any material from screener 18 with particles sized greater than about 1.75 inches is preferably fed via line 20 to crusher 22, wherein it is crushed to sizes smaller than 1.75 inches and then fed via line 24 to crusher 26. By contrast, material from screener 18 with particles smaller than 1.75 inches is preferably fed directly via line 28 to crusher 26.

Crusher 26 preferably further reduces the size of the limestone particles to a top size of 0.625 inches. The "−⅝ fragment" is then preferably fed to multi deck screener 30 via line 29.

Multiple deck screeners are well known to those skilled in the art; reference may be had to U.S. Pat. No. 5,341,939, the entire disclosure of which is hereby incorporated by reference into this specification. This patent claims (in claim 1 thereof) "1. A vibrating screen apparatus for material screening including in combination: a frame; at least first and second elongated vibrating screen decks having first and second sides and first and second ends; first and second pivot means for pivotally mounting the first ends of said first and second vibrating screen decks, respectively, on said frame, with said first vibrating screen deck located above said second vibrating screen deck; first and second means coupled with first and second said vibrating screen decks, respectively, for rotating said first and second vibrating screen decks about said first and second pivot means for varying the angle of said first and second vibrating screen decks relative to said frame; means for vibrating said first and second vibrating screen decks; and flexible curtain members extending between the first sides and the second sides, respectively, of said first and second vibrating screen decks to ensure that material falling through said first vibrating screen deck drops onto said second vibrating screen deck."

U.S. Pat. No. 5,341,939, in column 1 thereof, discusses other multiple deck screeners. It is disclosed in such column 1 that, "Vibrating material sorting screens are used in a variety of applications, including sand and gravel businesses and in mining operations. Such vibrating screens are used to sort material size, and typically comprise an elongated deck, which slopes downwardly from the feed end to the material delivery end. Usually, the decks are mounted in a deck holding frame, which, in turn, is supported on springs extending to a platform on a support surface. An eccentric vibrator is employed to vibrate the frame on the springs to cause a shaking of the material poured onto the vibrating screen deck to facilitate the movement of the material down the deck, and to expedite the material separation. Both the aperture of the screen and the size of the deck determines the separation size of the materials, and any material which is larger than the screen aperture finally is supplied from the end of the deck to a suitable receptacle. All material which is smaller than the screen aperture falls through the deck for further separation or processing."

U.S. Pat. No. 5,431,939 also discloses (in such column 1) that: "In some mining applications, the vibrating screen apparatus has two decks located one above the other, with the larger screen aperture on the top deck and a smaller screen aperture on the lower deck. In the sand and gravel business, three to five decks frequently are used, with the decks progressing in screen aperture from the largest at the top to the smallest at the bottom. Usually, all of these decks are mounted together in a single frame, vibrated by a single vibrating apparatus. The slope of each deck, from the feed end or material receiving end to the delivery end, is fixed once the vibrating screen apparatus is assembled. In addition, a single vibrating weight and drive motor is used; so that the magnitude and frequency of vibration of the entire unit is the same."

U.S. Pat. No. 5,431,939 also discloses (in such column 1) that, "When a multiple deck vibrating screen unit is employed, the magnitude and frequency of the vibration necessarily is a compromise between the optimum magnitude and speed of vibration required for the deck separating the larger size materials and the magnitude and speed of vibration required for the deck which is separating the smaller sized materials. In addition, the rate at which materials traverse the deck from the feed end to the delivery end varies, depending upon the size of the material; so that a compromise generally is made in the slope of the decks during the manufacturing of a multiple deck unit. In some cases, the slope angle of the different decks can be made to vary relative to one another; but once the unit is made, the different slope angles cannot further be adjusted in a typical deck."

U.S. Pat. No. 5,341,939 also discloses that, "When multiple deck units having three or more decks are employed, the compromises, which must be reached between the slope or angle of the different decks and the magnitude and speed of the vibrator, result in ever greater departures from the optimum, which would be desired for each deck having a single screen size. In view of this, it is desirable to provide a vibrating screen apparatus for a multiple deck unit which may be operated with each deck vibrated independently of the others, and where the angle or slopes of the decks may be independently varied, as desired."

One preferred multideck screener is the "Multi-Vib Screener" sold by Midwestern Industries, Inc. of Masillon, Ohio. This screener is described on the website for Midwestern Industries as follows: "Until recently, vibrating screens were calculated by using only two dimensions—width determined capacity and length determined efficiency. Midwestern Industries' Multi-Vib screens utilize a third dimension—'depth'—in addition to width and length to calculate size."

It is also disclosed on such website that, "The 'depth' dimension is accomplished by using five screening decks arranged one above the other to impart rapid vertical movement to the material being screened. The material passes through the top coarse screen to the progressively smaller screen openings below where it is retained—or passes through the finest screen on the fifth deck. . . . Multi-Vib units are available in three models . . . . They are powered by belt-free vibrating motors . . . ."

Referring again to FIG. 1, and to multideck screener 30, it is preferred that such multideck screener 30 comprise a 4 mesh screen, an 11 mesh screen, and 18 mesh screen, a 24 mesh screen, and a 32 mesh screen.

Referring again to FIG. 1, a portion of the material screened in multideck screener 30 may be fed via line 32 to air flow separator 34, in which the concentration of "fines content" of such material (i.e., the particles smaller than 250 microns) is reduced.

Airflow separators are well known to those skilled in the art, and they are referred to in the claims of U.S. Pat. Nos. 5,541,831 (computer controlled separator device), 5,943,231 (computer controlled separator device), 6,351,676 (computer controlled separator device), and the like. The entire disclosure of each of these United States patents is hereby incorporated by reference into this specification.

Air separators are also discussed in U.S. Pat. Nos. 3,772,857 (water air separator), 3,874,444 (duo-baffle air separator apparatus), 3,877,454 (air separator), 3,962,072 (air separator apparatus), 4,662,915 (powder air separator), 4,824,559 (rotary air separator), 5,244,481 (vertical air separator), 5,788,727 (centrifugal air separator), 6,053,967 (air separator), 6,664,479 (method and air separator for classifying charging material reduced in size), and the like.

Referring again to FIG. 1, and to the preferred embodiment depicted therein, the material fed from air flow separator 34 via line 38 preferably ranges in particle size from about 100 to about 2,500 microns, with at least 60 weight percent of the particles having sizes in the range of from about 600 to about 1400 microns. In one embodiment, at least about 70 weight percent of the particles have sizes in the range of from about 600 to about 1400 microns. In another embodiment, at least about 80 weight percent of the particles have sizes in the range from about 600 to about 1400 microns. In yet another embodiment, at least about 85 weight percent of the particles have sizes in the range of from about 600 to about 1400 microns.

In one embodiment, the material fed from airflow separator 34 (via line 38) ranges in particle size from about 500 to about 2500 microns (and, more preferably, from about 500 to about 2,000 microns). The airflow separator 34 preferably reduces the "fines content" of the particle compact so that the output in line 38 contains less than about 4 weight percent of particles smaller than 250 microns (60 mesh) and, more preferably, less than about 3 weight percent of particles smaller than 250 microns. In one embodiment, the material fed via line 38 contains less than 2 weight percent of material smaller than 250 microns and, more preferably, less than about 1 weight percent of material smaller than about 250 microns. In one embodiment, the material fed via line 38 contains less than about 0.4 weight percent of material smaller than 250 microns.

In one embodiment, the material fed from airflow separator 34 contains at least 95 weight percent of particles smaller than 3,350 microns.

In one embodiment, the material fed from air low separator 34 contains at least 95 weight percent of particles smaller than 2,360 microns.

In one embodiment, the material fed from airflow separator 34 contains at least 95 weight percent of particles smaller than 1,700 microns.

In one embodiment, the material fed from airflow separator 34 contains at least 60 weight percent of particles smaller than 1,000 microns.

In one embodiment, the material fed from airflow separator 34 contains at least 30 weight percent of particles smaller than 850 microns.

In one embodiment, the material fed from airflow separator 34 contains at least 3 weight percent of particles smaller than 600 microns.

In one embodiment, the material fed from airflow separator 34 contains at least 97 weight percent of particles greater than 425 microns.

In one embodiment, the material fed from airflow separator 34 contains at least 98 weight percent of particles greater than 300 microns.

In one embodiment, the material fed from airflow separator 34 contains at least 98 weight percent of particles greater than 250 microns.

In one embodiment, the material fed from airflow separator 34 contains at least 99 weight percent of particles greater than 212 microns.

In one embodiment, the material fed from airflow separator 34 contains at least 99.5 weight percent of particles greater than 180 microns.

Referring again to FIG. 1, and to the preferred embodiment depicted therein, a portion of the material produced in airflow separator may be periodically withdrawn via line 36 to laboratory 40, in order to test the particle size distribution of such material; similarly, material may be withdrawn from mixer 45 to lab 40. The particle size analysis may be conducted by conventional means. Reference may be had, e.g., to pages 92-109 of Barry A. Wills "Mineral Processing Technology," Sixth Edition (Butterworth Heinemann, Oxford, 1997. Reference also may be had, e.g., to U.S. Pat. Nos. 4,288,162 (measuring particle size distribution), 4,736,311 (particle size distribution measuring apparatus), 4,742,718 (apparatus for measuring particle-size distribution), 5,094,532 (method and apparatus for measuring small particle size distribution), 5,164,787 (apparatus for measuring particle size distribution), 5,185,641 (apparatus for simultaneously measuring large and small particle size distribution), 5,578,771 (method for measuring particle size distribution), 5,682,235 (dry particle-size distribution measuring apparatus), 6,191,853 (apparatus for measuring particle size distribution and method for analyzing particle size distribution), 6,252,658 (particle size distribution measuring apparatus), 6,281,972 (method and apparatus for measuring particle size distribution), 6,864,979 (particle size distribution measuring apparatus), and the like. The entire disclosure of each of these United States patents is hereby incorporated by reference into this specification.

Referring again to FIG. 1, two mixers (mixer 45 and mixer 44) are shown in the preferred process depicted. Mixer 44 is preferably used to add pigmented coating material to the mineral composition, and is preferably used on darkened headlap material. In any event, it is preferred to feed all of the mineral composition material first to mixer 45 and add (in one embodiment) adhesion promoter material in mixer 45.

Referring again to FIG. 1, the material fed via line 38 to mixers 45 and 44 preferably has the desired particle size distribution and a distribution modulus of from about 0.08 to about 0.14. If either or both of these values are not as desired, they may be adjusted by adding to mixer 44 more particulate material After such addition, and appropriate mixing, sampling of the material in mixer 44 may occur, and the process may be repeated until the desired values have been obtained.

Once the desired particle size distribution in mixer 44 has been obtained, and after such particles have preferably been pretreated with a pigmented material, one may pass such particles to mixer 45 in which one may add a mixture of oil and antistrip agent via line 47 to coat the inorganic particles in such mixer. Alternatively, one may add either the oil alone, or the antistrip agent alone, or neither the oil nor the antistrip agent. The goal, in one embodiment, is to produce a coating on such particulate matter with a thickness of from about 200 to about 2000 nanometers and, preferably from about 300 to about 1200 nanometers.

Preferred Adhesion Improving Additives

By way of yet further illustration, one may use the adhesion improving additives ("antistrip agents") disclosed in U.S. Pat. No. 4,038,102, the entire disclosure of which is hereby incorporated by reference into this specification. Claim 1 of this patent describes, "1. An additive for improving the adhesion of asphalt to aggregate comprising an ether amine having the general formula: [Figure] wherein: R1 is a hydrocarbon group having from about six to about sixteen carbon atoms, selected from the group consisting of alkyl and alkenyl; R2, r3, r4 and R5 are selected from the group consisting of hydrogen and alkyl radicals having from one to about two carbon atoms; n1 and n2 are numbers within the range from one to about four; x1 and x2 are numbers within the range from zero to about five, the sum of x1 and x2 being from one to five; the total number of carbon atoms in each [Figure] unit being from one to about four; and an alkanolamine having the formula: [Figure] wherein: R6 and R7 are selected from the group consisting of hydrogen and alkyl groups having from one to about two carbon atoms; n3 is a number within the range from two to about four; x3 is a number within the range from one to about three; the total number of carbon atoms in each [Figure] unit being with the range from two to four." Some of the "ether amines" described by such formula include, e.g., " . . . octoxyethylamine, decoxyethylamine, dodecoxyethylamine, tetradecoxyethylamine, hexoxypropylamine, octoxypropylamine, nonoxypropylamine, decoxypropylamine, dodecoxypropylamine, tetradecoxypropylamine, palmityloxypropylamine, myristyloxypropylamine, hexyl dioxyethylene oxyethylamine, octyl trioxyethylene oxyethylamine, dodecyl tetraoxyethylene oxyethylamine, myristyl dioxyethylene oxypropylamine, octyl tetraoxyethylene oxypropylamine, dodecyl tetraoxyethylene oxypropylamine, octyl dioxypropylene oxypropylamine, decyl trioxypropylene oxyethylamine, tetradecyl tetraoxypropylene oxypropylamine, octyl oxypropylene oxypropylamine, palmityl tetraoxypropylene oxypropylamine, heptenyl oxypropylene oxypropylamine, decenyl dioxyethylene oxyethylamine, octenyl oxypropylene oxyethylamine, dodecenyl tetraoxypropylene oxypropylamine, octyloxybutylene oxbutylamine, decyl trioxybutylene oxybutylamine, dodecyl tetraoxybutylene oxyethylamine, palmityl dioxybutylene oxypropylamine, decyl tetraoxy propylene oxypropylamine, and dodecyloxy propylene oxyethylamine."

By way of further illustration, one may use the amine antistripping agent disclosed in U.S. Pat. No. 4,721,159, the entire disclosure of which is hereby incorporated by reference into this specification. Claim 1 of this patent describes, "1. An asphaltic composition comprising an asphalt admixed with an aggregate and at the interface between said asphalt and said aggregate the reaction product of an amine antistrip and an acid salt in an amount sufficient to bind said asphalt to said aggregate; said acidic salt being a divalent or trivalent metal salt of an inorganic acid." In the background section of this patent, it is disclosed that, "Various efforts to improve adhesion are detailed in patents such as U.S. Pat. Nos. 2,582,823 and 2,582,824 to Fowkes in which the amine type of antistripping agents or the use of acids and soaps, as well as the use of lime, are discussed and their disadvantages noted. In an attempt to improve these well-known problems, with respect to cut-back asphaltic compositions, there is disclosed a priming solution to be used to attain this better adhesion. For this purpose, Fowkes discloses using alkaline metal salts of certain inorganic acids to form a wet aggregate which is admixed with the cut-back asphalt. Such priming solution does not give the necessary adhesion, does not work with all types of aggregates and does not work satisfactorily with hot-mix asphaltic compositions. Under the press of heavy traffic the resultant compositions crack and lose whatever alleged antistripping function they possess. U.S. Pat. No. 2,469,728 describes another effort to improve the adhesion of the asphalt to the mineral aggregate consisting of mollusk shells in which the shells are first treated with a dilute solution of a strong mineral acid and the thus treated aggregate then coated with asphalt. Here again, such is limited to a cut-back asphalt as set forth in column 1."

By way of yet further illustration, one may use one or more of the compositions claimed in U.S. Pat. No. 5,064,571, the entire disclosure of which is hereby incorporated by reference into this specification. This patent claims (in claim 1 thereof), "Mixtures of amido-amines prepared by a process comprising reacting at least one first component comprising at least one compound selected from the group consisting of mono- and dicarboxylic acids and acid esters, with a second component comprising polyoxyalkyleneamine bottoms products, where the reaction is conducted in the temperature range from about 25° to about 280° C. and at a pressure in the range from about atmospheric to about 200 psig."

By way of further illustration, one may use one or more of the hydroxylamines described in U.S. Pat. No. 6,290,772, the entire disclosure of which is hereby incorporated by reference into this specification. This patent claims (in claim 1 thereof), "1. A hydraulic cement composition comprising a mixture of Portland cement and, in an amount of up to 0.1 percent by weight of said cement, an hydroxylamine selected from the group consisting of N,N-bis(2-hydroxyethyl)-2-propanolamine and N,N-bis(2-hydroxypropyl)-N-(hydroxyethyl) amine, said amount being effective to enhance the compressive strength of the cement composition after 1, 3, and 7 days." In the "background" portion of this patent, some other amines which also may be used are described. It is disclosed that, "Various other additives may be added to cement to alter the physical properties of the final cement. For example, alkanolamines such as monoethanolamine, diethanolamine, triethanolamine and the like are known to shorten the set time (set accelerators) as well as enhance the one-day compressive strength (early strength) of cements. However, these additives have little beneficial effect on the 28-day set strength of the finished cement and in some cases may actually diminish it. This behavior is described by V. Dodson, in "Concrete Admixtures," Van Reinhold, N.Y., 1990, who states that calcium chloride, the best known set-time accelerator and early-age strength enhancer reduces compressive strengths at later-ages."

U.S. Pat. No. 6,290,772 also discloses that "U.S. Pat. Nos. 4,990,190, 5,017,234 and 5,084,103, the disclosures of which are hereby incorporated by reference, describe the finding that certain higher trihydroxyalkylamines such as triisopropanolamine (hereinafter referred to as "TIPA") and N,N-bis (2-hydroxyethyl)-2-hydroxypropylamine (hereinafter referred to as "DEIPA") will improve the late strength (strength after 7 and 28 days of preparation of the wet cement mix) of Portland cement, especially Portland cements containing at least 4 percent C4 AF. The strength-enhancing higher trihydroxyalkylamine additives described in these patents are said to be particularly useful in blended cements."

By way of yet further illustration, one may use one or more of the "organic modifiers" disclosed in U.S. Pat. No. 6,503,740, the entire disclosure of which is hereby incorporated by reference into this specification. Claim 1 of this patent describes, "1. A self-cleaning treatment media capable of acting upon at least one chemical contaminant in an aqueous composition assisting in the decomposition of that contaminant to at least one suitable lower molecular weight compound, the treatment media comprising: a mineral-based substrate present in granular form, the mineral-based substrate being a charged material selected from the group consisting of clays, clay analogs, synthetic resins and mixtures thereof; a compound capable of providing organic surface modification to a portion of the mineral-based substrate, the organic modification compound comprising quaternary amines, wherein the quaternary amines are selected from the group consisting of ditallow dimethyl ammonium chloride, hexadecyl ammonium chloride, octadecyl ammonium chloride, dimethyl di-hydrogenated tallow ammonium chloride, dicocodimethyl ammonium chloride, and mixtures thereof, and wherein the mineral-based substrate contains the organic modification compound; and at least one strain of microbial material engrafted on the surface of the mineral-based substrate containing the organic surface modification compound, the microbial material capable of facilitating decomposition of the at least one chemical contaminant in the aqueous composition; wherein the strain of microbial material has a biological activity, and wherein the organic surface modification compound is one which permits sufficient biological activity of the microbial material when the microbial material and the organic surface modification compound are both present on the mineral-based substrate."

U.S. Pat. No. 6,503,740 also discloses how to modify the mineral-based substrate, stating that, "The manner in which organic modification occurs can be by any method known to those skilled in the art. Heretofore, it was believed that quaternary amines used to modify the surfaces of the substrates such as those discussed previously were biocidal and would de-activate bacterial material which came into contact with the amine material. The present invention is predicated on the unexpected discovery that specific classes of quaternary amines are non-biocidal to target bacteria. Indeed, it has been found that the quaternary amines employed in the present invention provide actual enhancement to the bacterial colonies inoculated on the surface of the clay or mineral material. Without being bound to any theory, it is believed that this is due to the ability of the quaternary amine material to provide alcoholic materials such as isopropyl alcohol in nutrient level concentration when the quaternary amine is employed to organically modify the substrate materials; particularly those specified in the foregoing discussion."

U.S. Pat. No. 6,503,740 also discloses that, "The quaternary amine employed in the process of the present invention is one which will be biologically supportive of inoculated bacteria, i.e., not adversely effect bacterial activity when the quaternary amine is employed to provide organically modified clays and mineral materials. The preferred quaternary amine can be generally characterized as an ammonium compound having 12 to 18 carbon atoms. The quaternary amines employed in the present invention are preferably selected from the group consisting of organically modified hydrogenated tallow ammonium chlorides, ditallow dimethyl ammonium chloride, hexadecyl and octadecyl ammonium chloride and derivatives thereof. Most preferably, the quaternary amine is selected from the group consisting of di-methyl di-hydrogenated tallow ammonium chloride, dicocodimethyl ammonium chloride, and mixtures thereof."

U.S. Pat. No. 6,503,740 also discloses that, "In the preferred embodiment, the quaternary amine of choice is employed at a ratio sufficient to provide organic modification without adversely affecting biological activity of the target microbes or their ability to graft on the available surface of the mineral material. The preferred range of quaternary amine to clay or mineral material is between about 10% to 100% amine to clay or mineral respectively, with a range between about 10% to 45% and about 10 g to 100 g being preferred; and ranges between about 36 g to 100 g, and 48 g to 100 g being most preferred. In a preferred embodiment, the mineral-based substrate and the organic surface modification compound are present in a ratio between about 10 parts to about 100 parts; and about 5 parts to about 150 parts, surface modification compound to mineral-based substrate respectively."

U.S. Pat. No. 6,503,740 also discloses that, "In order to prepare the biologically activated organically modified mineral material of the present invention, quantities of the mineral or clay substrate material or resin and quaternary amine material are blended in any suitable manner, in the proportions defined above, together with precultured bacteria in an aqueous medium. Blending may be accomplished by various devices such as a ribbon blender, extruder or the like. Particulars about the production of organically modified clays are generally known in the art and are as outlined in U.S. Pat. No. 4,402,881 issued to Alther, which is incorporated by reference herein in its entirety. After suitable mixing, the resulting material which typically has a slurry-like consistency is dried and either milled to a powder or granulated."

U.S. Pat. No. 6,503,740 also discloses that, "During the mixing process, nitrogen supplying nutrients such as standard fertilizer, urea and the like or carbon/glucose supplying nutrients such as molasses and alcohol can be incorporated. If necessary, oxygenated material can also be incorporated by including slow-release sources of oxygen such as calcified seaweed or marl. Trace minerals can also be incorporated."

By way of further illustration, U.S. Pat. No. 6,786,963, the entire disclosure of which is hereby incorporated by reference into this specification, discloses certain diamide compounds that may be used in the process of the instant invention. Claim 1 of this patent describes "1. A paving composition comprising a bituminous material and a diamide compound, wherein: the composition is substantially free of water; and the diamide compound is represented by: [Figure] if A is hydrogen, B is R2 NHR3 NH2; if A is R2 NH2, B is R3 NH2; R1 is a branched or straight-chain alkyl or aromatic or alkylaromatic group; and R2 and R3 are the same or different and are a branched chain alkyl, straight-chain alkyl, or —R—NH—R, in which R is a branched chain alkyl with about 1 to about 6 carbon atoms or a straight-chain alkyl with about 1 to about 6 carbon atoms." This patent also discloses that, in its background section, that "Asphalt compositions have relatively poor adhesion to mineral aggregates in the presence of water. Since the aggregate is preferentially wetted by water, even if the aggregate is dry at the time it is blended with the asphalt, the eventual penetration of water into the composition reaches the aggregate and interferes with the bond between the aggregate and the asphalt. The result of this stripping is flaked pavement and potholes. Stripping problems also generally occur if the aggregate is poorly dried, if sandy carbonate aggregate containing a large amount of quartz particles is used, if carbonate aggregate is covered with dust, or if igneous (silicate) aggregates, such as granite, diorite, gabbro, diabase, or basalt, that strip in the presence of external water are used. To avoid such failures, adhesion-improving agents known as "anti-stripping agents" are commonly added to the asphalt. Before the mixing operation, these agents are added to the bituminous binder to reduce its surface tension and to induce on the binder an electrical charge opposite to that of the aggregate surface. Lower surface tension gives improved wettability of the aggregate, and charge reversal enhances bond strength by increasing Coulomb's attractive forces."

U.S. Pat. No. 6,786,963 also discloses that, "Cationic substances, particularly amines, have been traditionally used as anti-stripping agents. The cationic substances increase the hydrophobicity of the aggregate, making the aggregate resistant to the penetration of water so that water seeping into the asphalt does not tend to destroy the bond between the asphalt and the aggregate. The addition of the cationic substances tends to make the aggregate sufficiently water resistant that a good bond with the asphalt is formed. Among the cationic materials which have been used as adhesion promoters with asphalt, are primary alkyl amines (such as lauryl amine and stearyl amine) and alkylene diamines (such as the fatty alkyl substituted alkylene diamines). Because these amines may rapidly lose their activity when combined with asphalt and stored at elevated temperatures for an extended period, it has therefore been necessary to combine the amine with the asphalt at the work site when the asphalt is combined with the aggregate, which in practice presents difficulties in obtaining a homogeneous mixture. It is also noted that these amines are generally corrosive and may have an unpleasant smell."

U.S. Pat. No. 6,786,963 also discloses that, "Various asphalt formulations have been reported in attempts to enhance the properties of paving compositions while avoiding the above-described difficulties. U.S. Pat. No. 4,447,269 offers cationic oil in water type bituminous aggregate slurries. The emulsion comprises bitumen and a reaction product of a polyamine and a polycarboxylic acid, and water. Lime or cement can be added to reduce the setting time of the mixture."

As is also disclosed in U.S. Pat. No. 6,786,963, "U.S. Pat. No. 4,721,529 suggests the preparation and use of asphalt admixtures with the reaction product of an amine antistrip and an acid salt. The acid salt is a divalent or trivalent metal salt of an inorganic acid. U.S. Pat. No. 5,443,632 suggests cationic aqueous bituminous emulsion-aggregate paving slurry seal mixtures. The emulsifier is the product of reaction of polyamines with fatty acids and rosing, and a quaternizing agent. U.S. Pat. No. 4,806,166 proposes preparation of an aggregate comprising asphalt and an adhesion improving amount of an anti-stripping agent comprising the aminoester reaction product of a tall oil fatty acid and triethanolamine. The reaction product is of low viscosity, has good coating performance, and is inexpensive. U.S. Pat. No. 5,019,610 offers an asphalt composition comprising a blend of a thermoplastic rubber polymer and a fatty dialkyl amide, and asphalt cement. The preparation method requires only gentle stirring. The amide has a C6-C22 alkyl group attached to the carbonyl, and two C1-C8 alkyl groups attached to the amide nitrogen. The compositions offer good viscosities at relatively low residue percentages. The compositions are offered for use in road paving, asphalt roofing cements, mastics, moisture barriers, joint and crack fillers, and sheeting."

U.S. Pat. No. 6,786,963 also discloses that "U.S. Pat. No. 4,430,127 suggests preparation of a bitumen and epoxylated polyamine composition. The compositions provide improved adhesion between aggregate materials and the bitumen material. At least two of the amino nitrogen atoms are separated by six carbon atoms. U.S. Pat. No. 4,462,840 proposes use of a cation-active emulsifier which is the product of a polyamine and polycarboxylic acids. The emulsifier is useful in producing aqueous bituminous emulsion-aggregate slurries."

By way of yet further illustration, U.S. Pat. No. 6,875,341 describes and claims the use of certain antistrip agents; the entire disclosure of this United States patent is hereby incorporated by reference into this specification.

Claim 11 of U.S. Pat. No. 6,875,341 describes, "11. A process for extraction of selected heteroatom-containing compounds from hydrocarbonaceous oil for use in commodity, specialty or industrial applications, the process comprising contacting the hydrocarbonaceous oil with a mixture of polar solvent and water to selectively recover heteroatom-containing compounds into an extract fraction that contains low concentrations of non-heteroatom-containing compounds by use of a solvent and water mixture in a ratio to achieve a coefficient-of-separation of heteroatom-containing compounds that is greater than 65%, where the coefficient of separation is the mole percent of heteroatom-containing compounds from the carbonaceous oil that are recovered in the extract fraction minus the mole percent of non-heteroatom-containing compounds from the carbonaceous oil that are recovered in the extract fraction." An antistrip agent made via this process is identified in claim 12, which states, "12. The process of claim 11 wherein the extracted fraction containing high concentrations of heteroatom-containing compounds and low concentrations of non-heteroatom-containing compounds is used with little or no further processing as an antistrip asphalt additive . . . .". Similarly, claim 13 of U.S. Pat. No. 6,875,341 discusses, "13. The process of claim 11 wherein the extracted fraction containing high concentrations of heteroatom-containing compounds and low concentrations of non-heteroatom-containing compounds is used as a feedstock for manufacture of surfactants, pyridine N-oxides, quaternary pyridinium salts, asphalt antistrip additives . . . ."

By way of yet further illustration, one may use one or more of the antistrip agents disclosed in U.S. Pat. Nos. 4,839,404 (bituminous compositions having high adhesive properties), 4,933,384 (bituminous materials), 4,975,476 (bituminous materials), 5,352,275 (method of producing hot mix asphalt), 5,558,702 (asphalt emulsions containing amphoteric emulsifier), 5,566,576 (asphalt emulsions), 5,660,498 (patching system and method for repairing roadways), 5,667,577 (filled asphalt emulsions containing betaine emulsifier), 5,755,865 (asphalt rejuvenator and recycled asphalt composition), 5,766,333 (method for recycling and rejuvenating asphalt pavement), 6,093,494 (antistrip latex for aggregate treatment), 6,403,687 (antistrip latex for aggregate treatment), and the like. The entire disclosure of each of these United States patents is hereby incorporated by reference into this specification.

In one preferred embodiment, the antistrip agent is an organic amine, which may be primary, secondary, or tertiary, and which contains from about 1 to about 18 carbon atoms.

In one preferred embodiment, the antistrip agent is an amido-amine (fatty acid amine).

In one preferred embodiment, the antistrip agent is comprised of 4,4'-methylenebiscyclohexanamine. In another embodiment, the antistrip agent is comprised of mixed polycycloaliphatic amines.

In one preferred embodiment, in addition to or instead of the antistrip agent, one may use an adhesion-promoting agent, such as, e.g., the adhesion agents described in U.S. Pat. No. 5,240,760, the entire disclosure of which is hereby incorporated by reference into this specification. As is disclosed in this patent (see from line 56 of column 4 to line 38 of column 5), "Suitable adhesion agents are compound(s) capable of promoting the adhesion of roofing granules to an asphalt-based substrate. Preferred adhesion agents are hydrophobic in nature, and do not significantly alter the color of the roofing granules. The adhesion agent should be compatible with the polysiloxane and the roofing granules' surfaces. Preferred adhesion agents are silicones other than those that have long-chain hydrocarbon groups. Preferred silicones are described in E. Schamberg, Adhesion, v. 29(11), pp. 20, 23-27 (1985), as well as in U.S. Pat. Nos. 4,486,476, 4,452,961, 4,537,595 and 4,781,950. These kinds of silicones can be purchased under the trademark TEGOSIVIN (particularly TEGOSIVIN HL100) from Goldschmidt Chemical Corporation, Hopewell, Va."

U.S. Pat. No. 5,240,760 also discloses that, "Other adhesion agents that can be suitable include resin compositions R-20, R-24, R-27, R-270, and R-272, (Union Carbide Corporation, Danbury, Conn.), Wacker Silicone Resins MK, M-62 (Wacker-Chemi GMBA, Alemania, Germany), Dri-Sil™73, Dow Corning 1107, Dow Corning 477 Resin (Dow Corning Corporation, Midland, Mich.), SR-82 and SM 2138 available from General Electric, Schenectady, N.Y., and oleic acid, Witco Chemical Corporation, Chicago, Ill. Mixtures or combinations of adhesion agents may be employed."

U.S. Pat. No. 5,240,760 also discloses that, "The adhesion agent is employed on the roofing granules' surfaces to an extent sufficient to promote granule adhesion to an asphalt-based substrate. The amount of adhesion agent can vary depending on the composition of the roofing granules and adhesion agent. Generally speaking, adhesion agents are employed at about 0.01 to 5 pounds per ton of roofing granules (5×10−4 to 0.25 weight percent). In the case of TEGO-SIVIN silicones noted above, the adhesion agent is preferably applied to the roofing granules at about 0.5 to 1 lb. per ton of granules (2.5×10−3 to 0.05 weight percent), more preferably at 0.1 to 0.3 pound per ton (0.005 to 0.015 weight percent)."

U.S. Pat. No. 5,240,760 also discloses that, "The polysiloxane and adhesion agent are preferably applied to the roofing granules as solutes in an oil solvent. The oil assists in spreading the polysiloxane and adhesion agent to the roofing granules' surfaces, and also helps reduce dust formation."

U.S. Pat. No. 5,240,760 also discloses that, "When using an oil to apply the adhesion agent and polysiloxane to roofing granules' surfaces, the oil is employed at up to about 12 pounds per ton of roofing granules (0.6 weight percent) based on the weight of roofing granules, preferably 1 to 10 pounds per ton (0.05 to 0.5 weight percent), and more preferably 5 to 8 pounds per ton (0.25 to 0.4 weight percent)."

U.S. Pat. No. 5,411,803, the entire disclosure of which is hereby incorporated by reference into this specification, also describes adhesion agents. As is disclosed in such patent, "Adhesion to bituminous surfaces is also improved using ZFP and borate compounds. Adhesion is described in terms of wet and dry "pick tests," which are described in detail in the Test Methods Section. The dry and wet pick values have units of percent (%), with a higher number indicating better adhesion, a low number indicating cohesive failure of the bituminous surface to which the granule is adhered, rather than adhesive failure of the granule from the surface. Preferred values for dry pick are at least about 75%, whereas for wet pick the value is at least about 50%, more preferably at least about 70%." (See column 7, lines 3-14.)

Referring again to FIG. 1, and in the preferred embodiment depicted therein, the antistrip agent (and/or the adhesion agent) is mixed in mixer 45 with the particulate In one embodiment, the use of the antistrip agent is omitted, and only the oil is applied as a coating. In another embodiment, the use of the oil is omitted, and only the antistrip agent is applied as a coating. In yet another embodiment, neither such oil nor such antistrip agent is utilized.

The oil used may be, e.g., a "hydrocarbon oil," as that term is defined in U.S. Pat. No. 6,358,305, the entire disclosure of which is hereby incorporated by reference into this specification. At column 4 of U.S. Pat. No. 6,358,305, certain "hydrocarbon oils" are described; one or more of these "hydrocarbon oils" may be used in conjunction with the "antistrip agent" described elsewhere in this specification (or by itself) to prepare coated limestone granules. At lines 47-54 of such column 4, it is disclosed that, "The hydrocarbon oils employed in the compositions of the present invention may be either synthetic or natural in origin. These oils, referred to as process oils, can be obtained from petroleum, coal, gas and shale. The oils are of the lubricating oil viscosity range, typically in a 300 c.p. viscosity range. These hydrocarbon oils are often referred to as process oils and are available from several companies, such as Ergon Inc., Arco and Cross Oil Co."

Alternatively, or additionally, one may use one or more naphthenic mineral oils. These naphthenic mineral oils contain a significant proportion of naphthenic compounds, and they are well known to those skilled in the art. Reference may be had to the following United States patents which refer to "napthenic mineral oil" in their claims: U.S. Pat. Nos. 3,980,448 (organic compounds as fuel additives), 4,101,429 (lubricant compositions), 4,180,466 (method of lubrication of a controlled-slip differential), 4,324,453 (filling material for electrical and light waveguide communications cables), 4,374,168 (metalworking lubrication), 4,428,850 (low foaming lubricating oil compositions), 4,510,062 (refrigeration oil composition), 4,676,917 (railway diesel crankcase lubricant), 4,720,350 (oxidation and corrosion inhibiting additives for railway diesel crankcase lubricants), 4,793,939 (lubricating oil composition containing a polyalkylene oxide additive), 4,781,846 (additives for aqueous lubricant), 5,460,741 (lubricating oil composition), 5,547,596 (lubricant composition for limited slip differential of a car), 5,658,886 (lubricating oil composition), 6,063,447 (process for treating the surface of metal parts), 6,245,723 (cooling lubricant emulsion), 6,482,780 (grease composition for rolling bearing), 6,736,991 (refrigeration lubricant for hydrofluorocarbon refrigerants), and the like. The entire disclosure of each of these United States patents is hereby incorporated by reference into this specification.

When both the oil and the antistrip agent is used, it is preferred that the ratio of the oil/antistrip agent used is from about 10/90 to about 90/10 weight percent. In one embodiment, from about 0.25 to about 1.0 pounds of such oil is added for each 2,000 pounds of the limestone granules in mixer 45. In another embodiment, from about 0.25 to about 1.0 pounds of a mixture of such oil and one or more of the aforementioned antistrip agent is added for each 2,000 pounds of the limestone granules in mixer 45.

In another embodiment, from about 1 to about 3 parts of oil are preferably used for each part of the antistrip compound. In one aspect of this embodiment, from about 1.5 to about 2.5 parts of oil are used for each part of the antistrip compound.

In one embodiment, from about 0.5 to about 2.0 gallons of such oil, and from about 0.5 to about 1.0 gallons of such antistrip compound are added for each ton of the limestone granules.

In one embodiment, a sufficient amount of oil and/or antistrip agent is charged via about 2,000 nanometers and, preferably, from about 300 to about 1200 nanometers.

In one preferred embodiment, a blend of the oil and the antistrip compound is transferred through a blending screw. The rate of addition is preferably based on the rate of the atomizer as it relates to the rate of the material being transferred through the blending screw.

In one preferred embodiment, and referring again to FIG. 1, from about 0.001 to about 4 parts (by weight) of such oil, and from about 0.001 to about 4 parts (by weight) of such antistrip agent, are charged to mixer 45 for each 100 parts of particulate in such mixer. In one aspect of this embodiment, less than 2 weight percent of each of the oil and the antistrip agent are used. In another aspect of this embodiment, less than 1 weight percent of each of the oil and the antistrip agent are used. In yet another embodiment, less than about 0.5 weight percent of each of the oil and the antistrip agent are used.

In one embodiment, the oil and the antistrip agent are preferably mixed in mixer 45 which, in one aspect of this embodiment, is comprised of a blending screw. One may use any of the blending screws known to those skilled in the art. Reference may be had, e.g., to U.S. Pat. Nos. 3,881,708 (mixing extruders), 3,938,469 (apparatus for coating particulate material with finely divided solids), 5,573,331 (multiple-stage screw for blending materials), and the like. The entire disclosure of each of these United States patents is hereby incorporated by reference into this specification.

Samples may be periodically withdrawn from the mixer 45 via line 49 to be tested in laboratory 40 and to determine whether the coated particles have met the specifications for the roofing granules.

In one embodiment, illustrated in FIG. 1, the aforementioned antistrip agent and/or oil are charged to mixer 45 via line 47. In this embodiment, the particles from air flow separator 34 are charged directly via line 39 to mixer 45.

In another embodiment, illustrated in FIG. 1, the particles from air flow separator 34 are charged via line 38 to mixer 44, but a mixture of pigment and binder is added to mixer 44. The pigmented particles produced in mixer 44 are then charged via line 50 to mixer 45, wherein the antistrip agent and/or oil is added via line 47. Thereafter, the particles so treated are feed via line 51 to mass flow silo 52.

In one embodiment, the coated particles of this invention are tested to determine whether they have the required degree of hydrophobicity. One may utilize the assembly 100 depicted in FIG. 2 for this purpose.

Figure 2:
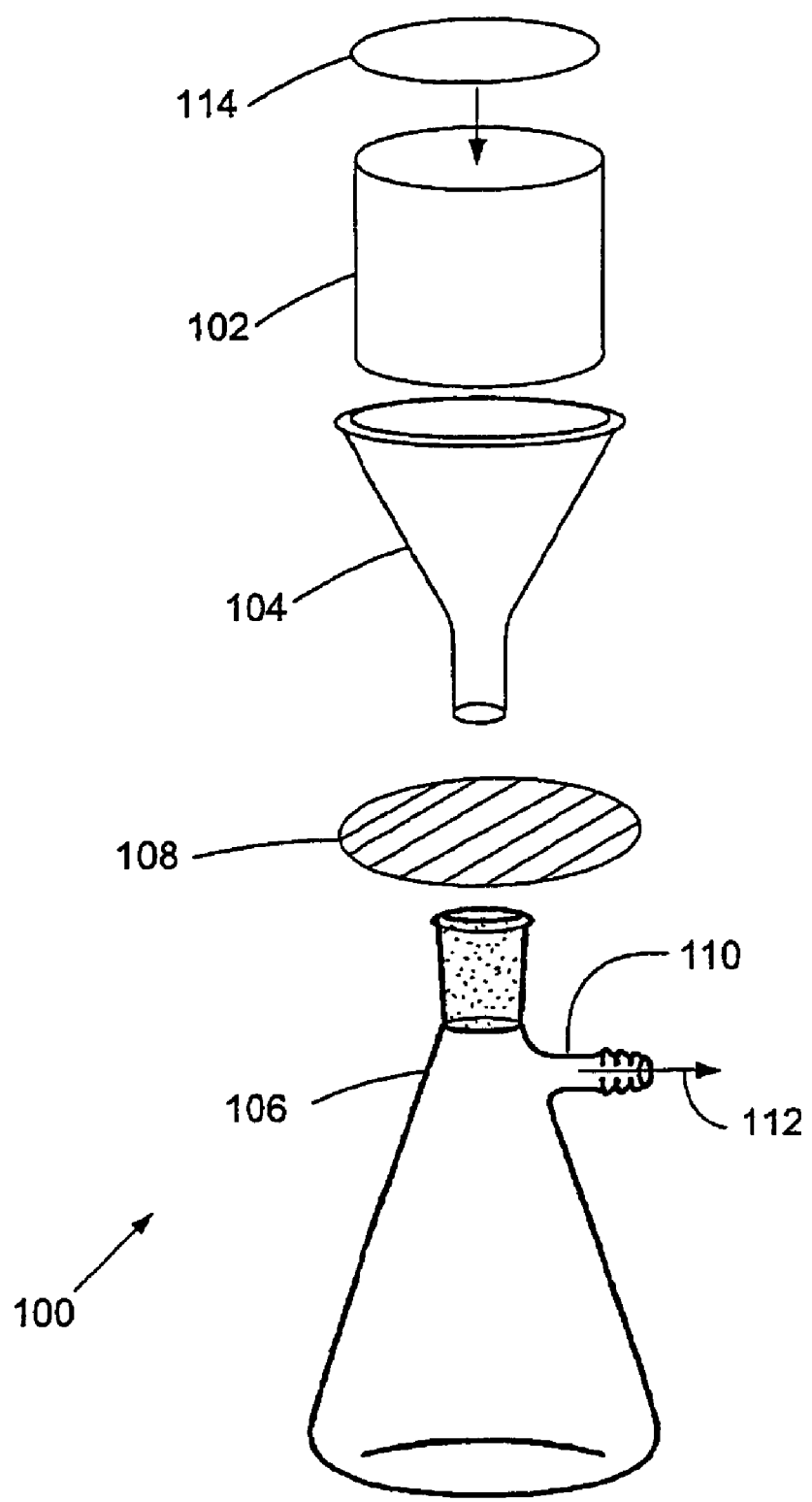
FIG. 2 is a schematic of a test apparatus for determining the hydrophobicity of the coated particles of this invention.

Referring to FIG. 2, and in the preferred embodiment depicted therein, the assembly 100 tests material for its ability to resist moisture adsorption, in accordance with the procedure described below. Prior to conducting the test, all of the materials and the equipment are preferably dried until they are substantially moisture free.

Utilizing a 5.5 centimeter round flat bottomed filter case 102 and an accompanying fitted funnel bottom 104, one may assemble the apparatus depicted onto a rubber-stoppered Buchner flask 106. In the embodiment depicted, a rubber disk 108 is preferably disposed on top of the Buchner flask 106 in order to seal the vacuum applied to such flask.

Referring again to FIG. 2, the vacuum is pulled through port 110 in the direction of arrow 112 via a vacuum pump (not shown). While a vacuum is pulled on the apparatus via a vacuum pump (not shown), a filter pad 114 (such as, e.g., a Whatman 40 gravimetric analysis filter pad) is wetted with water until it is fully wetted. Thereafter, the vacuum is allowed to remove free moisture from the filter pad.

Thereafter, the flat-bottomed filter case 102 and wetted filter pad are removed, and any free moisture from the bottom side of the filter assembly is also removed. The assembly is weighed, and the weight is recorded. Fifty (50) grams of the granular material to be tested is weighed to the nearest $100^{th}$ of a gram. This material is then transferred to the filter assembly without moving the filter pad on the bottom of the assembly, and the 50 grams of material are gently tapped to flatten out the sample. Thereafter, 100 grams of distilled water are weighed to the nearest $100^{th}$ of a gram; and the 100 grams of water are carefully poured (to avoid causing dimpling of the sample) onto the 50 grams of material which has been assembled back onto the top of the funnel assembly and is under vacuum. The vacuum is allowed to continue pulling the water through the material and through the filter pad. When the water stops coming from the filter (end point is reached when water is not visible on top of the sample and water has stopped being seen on the end of the funnel assembly for 30 seconds), the vacuum is broken and the filter assembly removed from the funnel assembly. Free moisture is then removed from the bottom of the filter assembly. The filter assembly and the wet sample are then weighed again, and the weight is recorded. The weight of the final assembly minus the (weight of dry filter assembly and wetted filter+weight of sample) is equal to the amount of water adsorbed onto the surface of the sample. This final weight of absorbed water is the reported value and can be reported as an absolute value or as a percentage of the weight of the sample being tested.

When this test is performed on treated and untreated limestone granules in the 10-30 mesh range, the untreated limestone will often absorb about 2.6 grams of water (which is 4.2 percent of the weight of the 50 gram sample). Some embodiments of the treated limestone, by comparison, will often absorb only 1.05 grams, which is only 2.1 weight percent of the 50 gram sample; other embodiments of the treated limestone have even greater degrees of hydrophobicity.

It is preferred that the granules of this invention has a hydrophobicity of less than about 3.0 percent and, more preferably, less than about 2.5 percent. In one aspect of this embodiment, the granules have a hydrophobicity of less than about 2.0 percent and, more preferably, less than about 1.5 percent.

The Moh's Hardness of the Coated Granules

In one embodiment, and referring again to the coated particles produced in mixer 44 of FIG. 1, the Moh's hardness of the coated particles is from about 2.5 to about 3.5 and is often from about 2.9 to about 3.1. It should be noted that calcite, which is the predominant component of limestone, is 3.0 on the Moh's scale.

The Adhesion of the Coated Granules

In one preferred embodiment, the adhesion of the coated granules removed via that, when reference is made to "adhesion loss as determined by ASTM Standard test 4977-3," it is to be understood that such term refers to the adhesion loss of a shingle made in accordance with the specified procedure that has been subjected to the specified rub test. This rub test procedure is described elsewhere in this specification.

pH of the Granules

In one embodiment, the pH of the coated particles in mixer 44 and/or 45 is from about 8 to about 11 and, more preferably, from about 9 to about 11.

Referring again to FIG. 1, after the coated particles in mixer 44 and/or 45 have the desired combination of properties, they are conveyed via line 50 to mass flow silo 52. Such a mass flow silo is well known and is described, e.g., in the claims of U.S. Pat. Nos. 4,818,117 (apparatus for mixing bulk materials in dust, powder, or coarse grained form), 6,547,948, and the like. The entire disclosure of each of these United States patents is hereby incorporated by reference into this specification.

Preparation of a Roofing Shingle

Referring again to FIG. 1, and in one preferred embodiment depicted therein, in step 56 roofing shingles are prepared with the coated granules disposed in mass flow silo 52.

The roofing shingles may be made in accordance with the procedure described in U.S. Pat. No. 3,888,684, the entire disclosure of which is hereby incorporated by reference into this specification; alternatively, such shingle may be made in accordance with the procedure described elsewhere in this specification.

As is disclosed in United States patent, "The asphaltic roofing compositions in which the novel algicidal roofing granules of the present invention are incorporated are roofing shingles, rolled roofing, and the like, having an organic asphalt-saturated felt base that is coated with an asphalt of a higher softening point and surfaced with base mineral granules having the subject inner and outer color coatings thereon. The felt layer is customarily composed of wood fibers, either alone or in combination with paper pulp, repulped paper and/or rags, asbestos fibers, or the like. Such felts are generally referred to in the industry as roofing felts. The saturants most commonly employed to saturate the felt layer include residual oil, soft residual asphalt and soft blown petroleum asphalt, and mixtures thereof. Preferred saturants generally have a ring and ball softening point of approximately 120° to 130° F. and a penetration of approximately 60 at 77° F."

U.S. Pat. No. 3,888,684 also discloses that, "This saturated felt layer is then coated with an asphalt of a higher softening point and lower penetration from that of the saturant. Preferred materials will generally have a ring and ball softening point of approximately 175° to 260° F. and a penetration of approximately 10 to 50 at 77° F. Coating asphalts of this type include native and sludge asphalts, fatty acid pitches and the like. In accordance with customary practices in the art, this asphalt coating layer is commonly embedded with powdered or fibrous fillers of inorganic or organic origin, such as powdered silica (sand), limestone, slate dust, clay, etc., and mixtures thereof. Upon application of the asphalt coating to the saturated felt layer, the color coated roofing granules of the invention are applied to the asphalt layer surface, and the resulting roofing surface is then passed through suitable rollers and presses, quenched and otherwise treated and handled in accordance with conventional practice in the roofing industry." (See from lines 27-63 of column 12.)

One may use the process disclosed in U.S. Pat. No. 4,274,243 to make the roofing shingle; the entire disclosure of which is hereby incorporated by reference into this specification. Claim 1 of this patent describes, "1. A method of forming a laminated roofing shingle comprising: (a) providing an indefinite length of asphalt-impregnated, felted material; (b) adhering a coating of mineral granules to at least one surface of said felted material; (c) cutting said material in a repeating pattern along the longitudinal dimension of said material so as to form an interleaved series of tabs of pairs of overlay members, each said tab, defined by said step of cutting, being of substantially identical shape and the lower edge of each said tab being defined by a smoothly curving negatively contoured edge; (d) making pairs of underlay members in a similar manner as above but wherein the lower edges of the underlay members are defined by a substantially continuously curving sinuous cut having a uniform periodic shape and amplitude such that each pair of underlay members thus formed are substantially identical; and (e) laminating said underlay members to said overlay members so as to form a series of shingles having substantially the same overall shape, wherein said step of laminating further includes the step of positioning said negatively contoured edge of each said tab directly over a substantially correspondingly curving portion of the lower edge of each said underlay member so as to simulate a series of alternating ridges and valleys of a portion of a tile covered roof."

One may use one or more of the mats described in U.S. Pat. No. 4,634,622 to make the roofing shingle; the entire disclosure of such patent is hereby incorporated by reference into this specification. As is disclosed in such patent, "Asphalt shingles and roll roofing have been produced in the same general manner for many years. The industry initially used an organic fibrous mat or an asbestos fiber mat as the preformed carrier. Mats of this type contributed significantly to the strength and flexibility of the finished product. Normally they were saturated with unfilled asphalt for waterproofing purposes, then coated with a thickness of filled asphalt in which a layer of roofing granules subsequently was embedded. The asphalt layer acted as a further waterproofing layer and held the granules in place. The granules and the fillers in the asphalt layer also protected the asphalt against the deleterious action of ultraviolet rays."

U.S. Pat. No. 4,634,622 also discloses that, "Later, the industry began moving more to the use of fiberglass mats instead of the conventional organic fibrous mats or asbestos fiber mats. Because fiberglass mats are much more porous than the previously used mats, this change eliminated the need for asphalt saturant. Instead, filled asphalt previously used only for the coating layer was now used both to impregnate and to coat the mat. Thus the properties of the filled asphalt became more critical. In addition to its waterproofing and weather resistant characteristics, the filled asphalt had to contribute more to the strength of the product, providing stability against deformation at roof temperatures and withstanding stresses encountered in the manufacturing process. Also, it had to adequately resist stresses due to handling by workmen and encountered by environmental conditions such as wind loading and thermal stresses."

U.S. Pat. No. 4,634,622 also discloses that, "The filler which has been used by the industry is mineral in nature comprised, for example, of ground limestone, silica, slate, trap rock fines, and the like, and is present in the asphalt in substantial amounts. Typically, the filler used in these conventional roofing products has a specific gravity of between about 2.5 and about 3, which is several times more dense than the asphalt which it extends or displaces (the specific gravity of asphalt is about 1.0). Thus a filler content of about 60% by weight yields a filled asphalt having a specific gravity of about 1.7."

One may use the process described in United States patent U.S. Pat. No. 5,411,803 to make the roofing shingle. As is disclosed in such patent, "Bituminous sheet materials such as roofing shingles may be produced using the granules of the invention. Roofing shingles typically comprise materials such as felt, fiberglass, and the like. Application of a saturant or impregnant such as asphalt is essential to entirely permeate the felt or fiberglass base. Typically, applied over the impregnated base is a waterproof or water-resistant coating, such as asphaltum, upon which is then applied a surfacing of mineral granules, which completes the conventional roofing shingle." (See column 9, lines 47-57.)

Asphalt is preferably used to making the roofing shingles. As is disclosed on page 71 of George S. Brady et al.'s "Materials Handbook," Twelfth Edition (McGraw-Hill Book Company, New York, N.Y., 1986), asphalt is "A bituminous, brownish to jet-black substance, solid or semi-solid, found in various parts of the world. It consists of a mixture of hydrocarbons, is fusible and largely soluble in carbon disulfide. It is also soluble in petroleum solvents and turpentine. The melting points range from 32 to 38 degrees C. Large deposits occur in Trinidad and Venezuela. Asphalt is of animal origin, as distinct from coals of vegetable origin. Native asphalt usually contains much mineral matter; and crude Trinidad asphalt has a composition of about 47% bitumen, clay, and water. Artificial asphalt is a term applied to the bituminous residue from coal distillation mechanically mixed with sand or limestone."

Asphalt is also described in the claims of various United States patents, such as, e.g., U.S. Pat. Nos. 3,617,329 (liquid asphalt), 4,328,147 (roofing asphalt formulation), 4,382,989 (roofing asphalt formulation), 4,634,622 (lightweight asphalt based building materials), 4,895,754 (oil treated mineral filler for asphalt), 5,217,530 (asphalt pavements), 5,356,664 (method of inhibiting algae growth on asphalt shingles), 5,380,552 (method of improving adhesion between roofing granules and asphalt-based roofing materials), 5,382,449 (method of using volcanic ash to maintain separation between asphalt roofing shingles), 5,511,899 (recycled waste asphalt), 5,516,573 (roofing materials having a thermoplastic adhesive intergace between coating asphalt and roofing granules), 5,746,830 (pneumatic granule blender for asphalt shingles), 5,776,541 (method and apparatus for forming an irregular pattern of granules on an asphalt coated sheet), 5,795,622 (method of rotating or oscillating a flow of granules to form a pattern on an asphalt coated sheet), 6,095,082 (apparatus for applying granules to an asphalt coated sheet to form a pattern having inner and outer portions), 6,358,319 (vacuum treatment of asphalt coating), 6,358,319 (magnetic method and apparatus for depositing granules onto an asphalt-coated sheet), 6,465,058 (magnetic method for depositing granules onto an asphalt-coated sheet), and the like. The entire disclosure of each of these United States patents is hereby incorporated by reference into this specification.

Means for Generating an Algicide and/or a Bactericide In Situ

In one preferred embodiment, the mineral composition of the present invention is comprised of means for producing an algicide or a bactericide after being exposed to electromagnetic radiation. Such means are well known to those skilled in the art.

Such means may exit a "photodynamic action," i.e., upon irradiation with light they act as catalysts for the oxidation of various substrates with oxygen. Some of these "photodynamic catalysts" are discussed in column 1 of U.S. Pat. No. 4,530,924, the entire disclosure of which is hereby incorporated by reference into this specification. In the third full paragraph of such column 1, it is disclosed that: "It is known that certain dyes, for example eosin, Bengal Rose, methylene blue and others, have a so-called photodynamic action, i.e. on irradiation with light, they act as catalysts for the oxidation of various substrates with oxygen [see, for example, G. O, Schenck, Angew. Chem. 69, 579 (1957)]. Because of this property, the said dyes also have a certain antimicrobial action [see, for example, Venkataraman, The Chemistry of Synthetic Dyes, Volume 4 (1971) pages 502-505 and C. J. Wallis, J. L. Melnick, J. Bacteriol. 89, 41 (1965)]." As is disclosed in column 6 of such patent, the phthalocyanine compounds of this patent develop antimicrobial activity upon being irradiated by visible and/or infrared light. The wavelength of visible light is from about 400 to about 750 nanometers. Infrared radiation is the invisible portion of the electromagnetic spectrum that lies between about 0.75 and 1,000 microns; radiation in the near infrared (from about 0.75 to about 3 microns) produces a sensation of heat.

Such means may be a photocatalyst, as that term is defined in U.S. Pat. No. 5,541,096, the entire disclosure of which is hereby incorporated by reference into this specification. This patent discloses that algae, fungi, and bacteria may be killed when titanium oxy compounds (such as titanium oxides) are exposed to electromagnetic radiation. These titanium oxy compounds (and others) are discussed at column 4 of the patent, wherein it is disclosed that: "Photosemiconductor particles having photocatalytic function include known photocatalysts such as titanium oxy compounds, zinc oxide, tungsten oxide, iron oxide, strontium titanate, molybdenum sulfide, cadmium sulfide, and the like, which can be used alone or in combination of two or more. Particularly, preferred are titanium oxy compounds having a higher photocatalytic function, higher chemical stability and being harmless. As used in the present invention, the term 'titanium oxy compounds' refers to those so-called titanium oxide, hydrated titanium oxide, hydrous titanium oxide, metatitanic acid, orthotitanic acid, titanium hydroxide and the like, the crystal form of which is not critical. The titanium oxy compounds as above may be produced by any one of a variety of known methods . . . ."

By way of further illustration, one may use the photocatalytic hydrophilic coating compositions disclosed in U.S. Pat. No. 5,916,947, the entire disclosure of which is hereby incorporated by reference into this specification. This patent discloses that, when exposed to visible light, "aqueous aerated solutions containing zinc oxide pigment leads to the formation of hydrogen peroxide only when exposed to ultraviolet light of wavelengths greater than 400 nm . . . ." (see columns 1-2). By comparison, when exposed to "visible light" (i.e., electromagnetic radiation detectable by the eye, ranging in wavelength from about 400 to about 740 nanometers), the zinc oxide composition of this patent become toxic to life. This composition is described, e.g., in claim 1 of such patent, which describes: "1. A material useful for producing antifouling activity when incorporated into a carrier comprising: about between 20 wt. % and 60 wt. % of the total material weight of zinc oxide containing less than about 0.001% by weight of lead, cadmium and sulphur oxides and being obtained from colloidal zinc oxide so as to have a mean particle size of between 0.1 to 0.5 microns and a surface area between 1 to square meters per gram; a photosensitizer in photoelectric contact with zinc oxide and being present in a ratio of one part by weight or less of photosensitizer to four parts by weight zinc oxide, said photosensitizer having a solubility below five parts per million by weight in water and wherein said photosensitizer is surface coated onto said zinc oxide and is selected from the group consisting of fumed anatase, strontium titanate, bianthrone, azulene, zinc pyrithione, terthiophene, hypericin and mixtures thereof."

In one embodiment, the toxic agent precursor used in the mineral composition of this invention produces a toxic agent when subjected to electromagnetic radiation. As used herein, the term electromagnetic radiation refers to radiation emitted from vibrating charged particles. As is known to those skilled in the art, a combination of oscillating electrical and magnetic fields propagates through otherwise empty space with the velocity of light; the constant velocity equals the alternation frequency multiplied by the wavelength. Reference may be had, e.g., to U.S. Pat. Nos. 5,374,405 (rotating fluidized bed reactor with electromagnetic radiation source), 5,686,178 (metal coated substrate articles responsive to electromagnetic radiation), 6,183,727 (use of long wavelength electromagnetic radiation), 6,369,399 (electromagnetic radiation shielding material and device), 6,616,451 (electromagnetic radiation emitting toothbrush), 6,654,627 (method and device for recording polarized electromagnetic radiation of inactivated strain of pathogenic microorganisms), and the like. The entire disclosure of each of these United States patents is hereby incorporated by reference into this specification.

One may use the titanium oxide toxic agent precursor disclosed in U.S. Pat. No. 6,291,067, the entire disclosure of which is hereby incorporated by reference into this specification. In column 1 of such patent, it is disclosed that: "When titanium oxide is irradiated with light, an electron having a strong reducing action and a positive hole having a strong oxidizing action are generated and a molecular seed coming into contact therewith is decomposed by the oxidation-reduction action. Using such an action, namely, photocatalytic action of titanium oxide, organic solvents dissolved in water, environmental pollutants such as agricultural chemicals and surface active agents, or harmful substances in air or malodors can be decomposition-removed. This method utilizes only titanium oxide and light and can be repeatedly used, and moreover, the resulting reaction product is a harmless carbon dioxide or the like." Claim 1 of this patent describes: "1. An organic polymer fiber having an environmental clarification function, which has supported thereon a photocatalytic powder for environmental clarification, said powder comprising finely divided titanium dioxide particles having a coating of porous calcium phosphate formed on at least part of the surface of each finely divided titanium dioxide particle, wherein an anionic surface active agent is present at least on the interface between said coating of porous calcium phosphate and the finely divided titanium dioxide particle." In the experiments described in the Examples of such patent, and ultraviolet light source (i.e., a source of electromagnetic radiation with a wavelength of from about 1 to about 400 nanometers) was used.

One may use one of the "oxygen molecule absorbing/desorbing" agents disclosed in U.S. Pat. No. 6,294,247, the entire disclosure of which is hereby incorporated by reference into this specification. As is disclosed in column 1 of this patent, "$TiO_2$, $V_2O_5$, ZnO, $WO_3$, etc. have heretofore been known as substances which, when irradiated by ultraviolet radiation, cause oxygen molecules to be adsorbed to or desorbed from an organic compound such as a smelly constituent for promoting decomposition (oxidation) of the organic compound.... For photocatalytic particles such as $TiO_2$ particles to function effectively as a photocatalyst, it is necessary that the photocatalytic particles be irradiated with ultraviolet radiation and held in contact with a substance to be decomposed thereby such as a smelly gas or the like."

One may use a titanium dioxide photocatalyst having a monoclinic crystal structure that is disclosed in U.S. Pat. No. 6,306,796, the entire disclosure of whish is hereby incorporated by reference into this specification. Claim 1 of this patent describes: "1. A titanium dioxide photocatalyst having a monoclinic crystal structure; wherein said photocatalyst is irradiated with light of a wave length which has energy greater than a band gap of the photocatalyst." The materials that are degraded by the photocatalyst of this patent are described in column 2 of the patent and include: "Examples of deleterious materials which are decomposed or oxidized by photocatalytic reaction by use of titanium oxide and then removed, are materials having adverse effect upon human body and living environment, and materials which might have such adverse effect. For instance, there are a variety of biochemical oxygen demand materials; environmental pollution materials such as air pollution materials; materials of various agricultural chemicals such as herbicide, bactericide, insecticide and nematocide; and microorganism such as bacteria, actinomyces, funguses, algaes and molds. Examples of environmental pollution materials are organic halogen compounds, organic phosphorus compounds, other organic compounds, and inorganic compounds such as nitrogen compounds, sulfur compounds, cyanide and chromium compounds. Examples of organic halogen compounds are polychlorinated biphenyl, fleon, trihalomethanes, trichloroethylene, and tetrachloroethylene. Examples of organic compounds other than organic halogen compounds and organic phosphorous compounds are surface active agents, hydrocarbons such as oils, aldehydes, mercaptans, alcohols, amines, amino acid, and protein. Examples of nitrogen compounds are ammonia and nitrogen oxide."

One may use a crystalline toxic agent precursor such as, e.g., the crystalline titania disclosed in U.S. Pat. No. 6,362,121, the entire disclosure of which is hereby incorporated by reference into this specification. Claim 1 of such patent describes: "1. A substrate provided, on at least a portion of one of its faces, with a coating with a photocatalytic property based on titanium dioxide which exhibits an external hydrophilic surface, which is at least partially crystalline and which is incorporated in said coating partly in the form of particles predominantly crystallized in the anatase form, said particles being incorporated in the coating using an inorganic binder in the form of an amorphous or partially crystalline silicon oxide or a mixture of oxides comprising silicon oxides."

One may use one or more of the photocatalysts described in U.S. Pat. No. 6,368,668, the entire disclosure of which is hereby incorporated by reference into this specification. A process for producing at least some of these photocatalysts is described in claim 1 of such patent, which discloses: "1. A process for producing a functional material having photocatalytic activity, comprising the steps of: coating a photocatalyst coating composition comprising a photocatalytic metal oxide and/or a precursor of the photocatalytic metal oxide onto the surface of a substrate; and rapidly heating the surface of the coated substrate to fix the photocatalytic metal oxide onto the surface of the substrate, characterized in that: the rapid heating is carried out by a heating means provided with a heating element having a heating value per unit area of not less than 120 MJ/m2 hr, and the distance between the heating element and the surface of the substrate is 5 to 300 mm, and the rapid heating is carried out for 2 to 60 seconds."

One may use the ultrafine titanium dioxide powder disclosed in U.S. Pat. No. 6,383,980 to produce an algicidal agent; the entire disclosure of this patent is hereby incorporated by reference into this specification. This material is described in claim 1 of such patent, and it discloses: "1. A photocatalytic titanium dioxide powder comprising finely divided titanium dioxide particles each having supported on the surface thereof a first supported layer comprising a calcium compound, and further having supported on the surface of said first supported layer-formed titanium dioxide particle a porous second supported layer comprising a photocatalytically inactive and substantially water-insoluble substance."

One may use the pyrrole photosensitizer disclosed in U.S. Pat. No. 6,454,951, the entire disclosure of which is hereby incorporated by reference into this specification. Claim 1 of this patent describes: "1. A composition comprising a solid carrier and more than one photosensitizer comprising a tetrapyrrole and/or tetraazapyrrole compound, wherein the carrier is swellable in water and is selected from the group consisting of polystyrol, sephadex and clay, and wherein the more than one photosensitizer are chemically bonded to the carrier, have different absorption maxima, and are selected such that the entire spectrum of visible light is utilized for photosensitization." As is disclosed in columns 1 and 2 of such patent, such photosensitizer can be used to kill algae, yeast, fungi, germs, etc. As is disclosed in such column 1, "the terms, 'germs and/or microorganisms' relate to microbes, especially microbes which can be pathogeneous, as e.g. gram-positive, gram-negative bacteria, algae, yeast and fungi, wherein said germs can be present alone or in combination with other microorganisms."

One may utilize the photocatalytic composition disclosed in U.S. Pat. No. 6,683,023, the entire disclosure of which is hereby incorporated by reference into this specification. In column 1 of this patent, it is disclosed that many of the prior art algicides and bactericides in addition to killing pathogens, also attacks the organic material in which it is disposed. It is disclosed in such column 1 that: "In recent years, photocatalytic fine particles using titanium dioxide are attracting attention as an environmental cleaning material for antimicrobial, deodorization, antifouling, air cleaning, water cleaning and the like. The photocatalytic mechanism of titanium dioxide is considered attributable to the following mechanism. Upon irradiation of light on a titanium dioxide fine particle, an electron and a hole are generated inside the titanium dioxide fine particle, which reacts with water or oxygen in the vicinity of the surface of a titanium dioxide fine particle to generate hydroxy radical or hydrogen peroxide. As a result, strong oxidation reduction activity of this hydroxy radical or hydrogen peroxide, harmful organic substances are decomposed into carbon dioxide and water, and thereby cleaned. Such photocatalytic activity of a titanium dioxide fine particle is thought to semipermanently continue as long as a titanium dioxide fine particle, light, water and oxygen are present."

U.S. Pat. No. 6,683,023 also discloses that: "By taking advantage of this photocatalytic property of titanium dioxide, as a representative application example, titanium dioxide fine particles are being kneaded into an easily handleable medium, such as fiber or a plastic molded article, or into a coating on the surface of a substrate, such as cloth or paper. However, decomposition or deterioration by the strong photocatalytic activity of titanium dioxide readily occurs not only on harmful organic materials or environmental pollutants but also on the medium itself such as fiber, plastic or paper and this is an obstacle to durability in practical use. Due to easy handleability of the titanium dioxide fine particle, a coating material comprising a mixture of titanium dioxide fine particles and a binder has been developed. However, an inexpensive binder having durability sufficiently high to overcome, for example, decomposition or deterioration on the medium has not yet been found."

U.S. Pat. No. 6,683,023 also discloses that: "JP-A-9-225319 (the term "JP-A" as used herein means an "unexamined published Japanese patent application") and JP-A-9-239277 disclose means for preventing and suppressing the deterioration of a resin medium or the deterioration of a binder due to the strong photocatalytic activity of titanium dioxide particles. The proposed means is a method of allowing a photo-inactive compound having such as aluminum, silicon and zirconium to be supported on a titanium dioxide particle in an archipelago shape having a steric barrier to retard the photocatalytic activity. According to this method, the photo-inactive compound is supported in an archipelago shape; however, specific sites of the resin medium or the binder disadvantageously remain present under the strong photocatalytic activity of titanium dioxide."

U.S. Pat. No. 6,683,023 also discloses that: "International Publication WO99/33566 discloses a powder material of titanium dioxide fine particles, where a porous coating layer of calcium phosphate is formed on at least a part of the surface of a titanium dioxide fine particle and an anionic surfactant is present at the interface therebetween."

U.S. Pat. No. 6,683,023 also discloses that: "With respect to a slurry containing titanium dioxide having photocatalytic activity, JP-A-10-142008 discloses an anatase-type titanium oxide-containing slurry which is obtained by heat-treating a titania sol, a titania gel form or a titania sol-gel mixture in a closed vessel simultaneously with a pressurization treatment and then dispersing using an ultrasonic wave or stirring the treated product."

U.S. Pat. No. 6,683,023 also discloses that: "JP-A-11-343426 discloses a photocatalytic coating material having excellent dispersion stability and specifically discloses a photocatalytic coating material containing, in a solvent, a silica sol and titanium oxide having a Raman spectrum peak in the range of 146 to 150 cm-1 and being occupied by anatase type titanium dioxide in a ratio of 95% by mass or more."

One may coat the mineral composition of this invention with a photocatalytic coating such as, e.g., the coating described in claim 1 of U.S. Pat. No. 6,700,066, the entire disclosure of which is hereby incorporated by reference into this specification. Claim 1 of this patent describes: "1. A coated substrate prepared by a process comprising: (a) preparing a substrate for deposition with a coating, wherein the coating comprises crystallized particles of an oxide of a metal A having photocatalytic properties, a mineral binder comprising at least one oxide of a metal B having photocatalytic properties, optionally at least one oxide of a metal M devoid of photocatalytic properties, and optionally at least one silicon oxide; (b) depositing the coating onto a surface of the substrate, by depositing the coating from liquid-phase dispersions containing oxides of the metals A and B, optionally the oxide of metal M and optionally the silicon oxide, in a relative proportion by weight of the metals and Si given by A/(B+M+Si), the relative proportion ranging from 60/40 to 40/60; and (c) allowing the coating to set."

The coatings of U.S. Pat. No. 6,720,066 provide both photocatalytic performance and durability. As is disclosed in column 2 of such patent, "The present invention has allowed the simultaneous optimization of two coating properties, photocatalytic performance and coating durability, which previously appeared to be incompatible."

One may use a photocatalytic material having titanium oxide crystals and anions X incorporated therein, as is disclosed in U.S. Pat. No. 6,794,065, the entire disclosure of which is hereby incorporated by reference into this specification. Claim 1 of this patent discloses: "1. A photocatalytic material exhibiting a photocatalytic action when exposed to light with a wavelength in the region of ultraviolet light and visible light, comprising a titanium compound Ti—O—X obtained by at least one of: substituting an anion X for a plurality of oxygen sites of titanium oxide crystals, doping an anion X between lattices of a titanium oxide crystal, and doping an anion X in grain boundaries of titanium oxide aggregate." In column 1 of this patent, a discussion is presented as to why most titania materials exhibit photocatalytic activity only in the ultraviolet range. It is disclosed that: "Hitherto, known materials exhibiting a photocatalytic action include the likes of TiO2 (titanium dioxide), CdS (cadmium sulfide), WO3 (tungsten trioxide), and ZnO (zinc oxide). These photocatalytic materials are semiconductors, absorb light to form electrons and holes, and present various chemical reactions and bactericidal actions. However, because titanium oxide is nontoxic and is superior from the standpoint of stability to water and acid, so far only titanium oxide has been put to practical commercial use as a photocatalyst."

U.S. Pat. No. 6,794,065 also discloses that: "However, because of the values of the band gap (Eg=3.2 eV) of titanium oxide, the operating light of such a titanium oxide photocatalyst is limited to ultraviolet light with a wavelength .lambda.<380 nm. As a consequence, there remains an unfulfilled demand for development of materials which exhibit catalytic activity when irradiated with visible light with a wavelength of 380 nm or longer. These materials are desired, for example, for use indoors and for improving photocatalytic activity."

U.S. Pat. No. 6,794,065 also discloses that: "As described in Japanese Patent Laid-Open publication No. Hei 9-262482, by modifying materials using ion implanting of metal elements such as Cr (chrome) and V (vanadium) in anatase type titanium oxide having a high catalytic activity, the light absorbing edge of titanium oxide can be shifted to the long wavelength side to permit the operation of titanium oxide catalyst in visible light. No reports discussing the doping of Cr, V, and so on have been published since the early 1970s which succeeded in operating under visible light. Japanese Patent Laid-Open publication No. Hei 9-262482 describes that operation under visible light can be enabled through use of special techniques for doping Cr, V, and so on. Thus, in the above conventional example, the operation of TiO2 photocatalyst under visible light is made possible by a technique of ion implanting metal elements in TiO2. However, metal ion implantation is disadvantageous because of its high cost. While there is a demand for methods for manufacturing TiO2 photocatalyst, such as by synthesis in solution or by sputtering, when these methods are employed, the resulting photocatalysts can not be operated under visible light. It is generally considered that this is because Cr of the dopant aggregates or forms oxides such as Cr2 O3 in a crystallization process. Thus, in the conventional examples, there is a problem that a technique of ion implanting metal elements must be adopted in order for metal elements to be used to enable operation of TiO2 under visible light."

One may use a photocatalytic material that is activated by visible light such as, e.g., the material disclosed in U.S. Pat. No. 6,835,688, the entire disclosure of which is hereby incorporated by reference into this specification. As is disclosed in column 1 of this patent, "Conventionally known materials exhibiting a photocatalytic action include TiO2 (titanium dioxide), CdS (cadmium sulfide), WO3 (tungsten trioxide), and ZnO (zinc oxide), for example. These photocatalytic materials are semiconductors, absorb light to form electrons and holes, and also promote various chemical reactions and bactericidal actions. However, because titanium oxide is non-toxic and exhibits a superior stability to water and acid, thus far, only titanium oxide has afforded practical commercial use as a photocatalyst. However, because of the values of the band gap (Eg=3.2 eV) of titanium oxide the operating light of such a titanium oxide photocatalyst is limited to ultraviolet light with a wavelength .lambda.<380 nm. As a consequence, an unfulfilled demand exits for materials which exhibit catalytic activity when irradiated with visible light having a wavelength of 380 nm or longer. These materials are desired, for example, for use indoors and for improving photocatalytic activity."

U.S. Pat. No. 6,835,688 also discloses that: 'As described in Japanese Patent Laid-Open publication No. Hei 9-262482, by modifying materials using ion implanting of metal elements such as Cr (chromium) and V (vanadium) in anatase type titanium oxide having a high catalytic activity, the light absorbing edge of titanium oxide can be shifted to the long wavelength side to permit the operation of titanium oxide catalyst in visible light. Although a number of reports discussing the doping of Cr, and V, for example, on have been published since the early 1970s, these reports describe, however, that in instances where operation under visible light is enabled, the performance of the titanium oxide sharply lowers. On the other hand, as described in Japanese Patent Laid-Open publication No. Hei 9-262482, the original performance of titanium oxide can be maintained through use of special techniques for doping Cr, and V, for example. Thus, in the above conventional example, the operation of titanium oxide photocatalyst under visible light is made possible by ion implantation of metal elements in titanium oxide.'

A Durable Means for Inhibiting the Growth of Algae and Bacteria

In this section of the specification, one preferred means for inhibiting the growth of algae and bacteria will be described. The material used in this embodiment will provide long term durability to the mineral compositions and to the articles (such as shingles) into which such material is incorporated.

EXAMPLES

The following examples are used to illustrate the claimed invention but are not to be deemed limitative thereof. Unless otherwise specified, all parts are by weight, and all temperatures are in degrees Celsius.

In each of the following examples, roofing granules were used to make a sample shingle, and the sample shingle was then tested for granule adhesion in accordance with ASTM Standard Test 4977-3. The procedure for making the test samples is described hereinbelow.

The test samples used to determine the adhesive characteristics of the coated limestone granule particles were constructed using a petroleum-based roofing asphalt manufactured by the Hunt Refining Company of Tuscaloosa, Ala. This asphalt had been oxidized by blowing with air at a temperature of approximately 500 degrees Fahrenheit, to achieve a final Ring & Ball Softening Point of 215 degrees Fahrenheit (as determined by ASTM D 36) and had a Needle Penetration of between 15 decimillimeters at 77 degrees Fahrenheit (as determined by ASTM D 5). The asphalt product produced after the oxidation is hereinafter referred to as "asphalt shingle coating."

The viscosity of the asphalt shingle coating was determined in accordance with ASTM D 4402 at three different temperatures. The viscosities were 2558 centipoise at 350 degrees Fahrenheit, 500 centipoise at 400 degrees Fahrenheit and 189 centipoise at 450 degrees Fahrenheit.

A finely divided limestone filler, "grade 85-200 mesh shingle filler," was obtained from the Franklin Industrial Minerals Company Nashville, Tenn. This filler was blended with the "asphalt shingle coating" to a final level of 65 weight percent filler. This blended material is referred to hereinafter as "filled asphalt coating," and it had a final Ring & Ball Softening Point of 251 degrees Fahrenheit (as determined by ASTM D 36) as well as a Needle Penetration of decimillimeters at 77 degrees Fahrenheit (as determined by ASTM D 5).

The viscosity of the "filled asphalt coating," as determined by ASTM D 4402, was 6517 centipoise at 400 degrees Fahrenheit, 1867 centipoise at 450 degrees Fahrenheit, and 1133 centipoise at 475 degrees Fahrenheit.

The "filled asphalt coating" was then applied to a commercially available bonded non-woven glass roofing fabric with a dry weight of approximately 1.68 pounds per one hundred square feet. This fabric consisted of sized individual "E" Glass filaments of 15.25-16.5 microns in diameter ("M" fiber) and from 0.75-1.25 inches in length, which are randomly oriented and bonded with a modified urea-formaldehyde resin binder, which has been applied to a level of 20.8% (dry weight). This fabric was obtained from the Johns Manville Corporation of Denver, Colo.

The aforementioned glass fabric was coated on each side and saturated throughout with the aforementioned "filled asphalt coating" at a temperature of 425 degrees Fahrenheit by using a squeegee to force the coating into the glass fabric. After the glass fabric had been fully saturated with the "filled asphalt coating," 60 mils of such "filled asphalt coating" were applied to the top side of each sample sheet to form a coating. Thereafter, granule particles were sprinkled onto the coating as described hereinbelow.

Samples of treated, untreated and control granule particles produced for these experiments were immediately sprinkled on the top surface of the warm sheet(s); the granules were applied within no more than 5 minutes after the coating was applied. The granule particles were then roll pressed into the coated glass sheet using a 10 pound roller. The rolled-pressed samples were then allowed to cool to ambient temperature and thereafter were used for the adhesion experiments described hereinbelow.

After the finished sheets were cooled to ambient temperature, they were then cut into 2 inch by 9 inch sample specimens for further "rub-loss testing" in accordance with ASTM D 4977-03. Prior to such "rub-loss testing," loose granule particles were removed from the samples by gentle tapping of the specimens.

At least two sample specimens were cut for each trial variant, with the long dimension of the specimen in the machine direction or press-roll direction. Specimens were conditioned at room temperature of 73.4 degrees Fahrenheit plus or minus 3.6 degrees Fahrenheit) for at least 30 minutes before testing. Granule abrasion tests were conducted using a Granule Test Apparatus as described in ASTM Procedure D 4977-03. All loose granules were removed from the specimens by gentle tapping of the sample. Each specimen was weighed to the nearest 0.01 grams and a record was made of the initial weight of the specimen. The specimen was centered in the sample holder of the Test Apparatus with the mineral surface facing up and the long axis of the specimen aligned with the brush stroke of the Test Apparatus. The Test Apparatus was activated such that the specimen was abraded 50 complete cycles, each cycle consisting of a forward stroke and a back stroke, with the brush travel remaining parallel to the long axis of the specimen. The specimen was removed from the sample holder and any loose granules were removed from the sheet by gently tapping the sample. The specimen was weighed to the nearest 0.01 grams and a record was made of the final weight of the specimen. The difference in weights for multiple samples of the same specimen were calculated and averaged to determine the average granule loss by abrasion.

Examples 1-11

In the experiments described in Examples 1-11, ten different variants of treated limestone granule shingle specimens and one control specimen were tested upon completion of the fabrication of the test samples and after one week of moist storage to determine the relative granule rub-loss amounts under ASTM D-4977-03. For each set of conditions, rub loss results are reported for both un-aged samples, and aged samples (the aged samples being those that had been subjected to a water quench and stored in an un-dried state for one week.).

The limestone roofing granules used in these experiments of Examples 1-11 were obtained from the Franklin Industrial Mineral Corporation of Nashville Tenn. as "limestone headlap granules." They had a particle size distribution such that at least about 80 weight percent of said granules had sizes in the range of from about 600 to about 1400 microns, and less than about 4 weight percent of said headlap granules were smaller than 250 microns. These limestone granules were produced at the Anderson, Tenn. plant of the Franklin Industrial Mineral Corporation in substantial accordance with the procedure described elsewhere in this specification.

In the experiment of Example 1, the headlap granules were coated with 0.5 gallons per ton of a 50/50 mixture of an amido amines sold as "AD-HERE" LOF 6500" (sold by Arr Maz Custom Chemicals, Inc. of Winterhaven, Fla.) and "HYPRENE 100" naphthenic oil sold by Ergon Refining, Inc. of Jackson, Miss. This oil had a viscosity of from 100 to 115 Saybolt Universal Seconds (SUS), as measured by ASTM D445, an American Petroleum Institute (API) gravity at 60 degrees Fahrenheit of 24.6 (as measured by ASTM D1260), and a Cleveland Open Cup (COC) flash point of between 325 and 340 degrees Fahrenheit (as measured by ASTM D92). The un-aged sample produced with these headlap granules had a rub loss of 4.8 grams and the aged sample had a rub loss of 4.4 grams.

In the experiment of Example 2, the same mixture was used as specified in Example 1, but the application rate was 1.0 gallon per ton rather than 0.5 gallons per ton. The un-aged sample produced with these headlap granules had a rub loss of 4.5 grams, and the aged sample had a rub loss of 4.2 grams.

In the experiment of Example 3, the same mixture was used as specified in Example 1, but the application rate was 1.5 gallons per ton rather than 0.5 gallons per ton. The un-aged sample produced with these headlap granules had a rub loss of 3.8 grams, and the aged sample had a rub loss of 4.3 grams.

In the experiment of Example 4, the "AD-HERE" LOF 6500" was replaced with "AD-HERE" LOF 6500LS" amido-amine that was also obtained from Arr Maz Custom Chemicals, Inc. of Winterhaven, Fla. and was also applied as a 50/50 mixture at an application rate of 0.5 gallons per ton. The un-aged sample produced with these headlap granules had a rub loss of 4.7 grams, and the aged sample had a rub loss of 4.3 grams.

In the experiment of Example 5, the same mixture used in Example 4 was used, but the application rate was 1.0 gallon per ton. The un-aged sample produced with these headlap granules had a rub loss of 4.5 grams, and the aged sample had a rub loss of 4.7 grams.

In the experiment of Example 6, the same mixture used in Example 4 was used, but the application rate was 1.5 gallons per ton. The un-aged sample produced with these headlap granules had a rub loss of 4.9 grams, and the aged sample had a rub loss of 5.1 grams.

In the experiment of Example 7, the same amido-amine was used, but none of the oil was used. The application rate was 1 gallon per ton of such amine. The un-aged sample produced with these headlap granules had a rub loss of 4.4 grams and the aged sample had a rub loss of 4.9 grams.

In the experiment of Example 8, the same oil was used, but none of the amido-amine was used. The application rate was 1 gallon per ton of such oil. The un-aged sample produced with these headlap granules had a rub loss of 4.2 grams and the aged sample had a rub loss of 4.4 grams.

In the experiment of Example 9, the mixture described in Example 1 was used at an application rate of 1.75 gallons per ton. The un-aged sample produced with these headlap granules had a rub loss of 3.7 grams.

In the experiment of Example 10, the mixture of Example 1 was used at an application rate of 2.0 gallons per ton. The un-aged sample produced with these headlap granules had a rub loss of 4.6 grams.

In the control experiment of Example 11, neither such oil nor an amine (or other anti-strip agent) was used. The un-aged sample produced with these headlap granules had a rub loss of 4.8 grams, and the aged sample had a rub loss of 4.2 grams.

Although applicants do not wish to be bound to any particular theory, it is believed that the combination of the oil and the antistrip agent used in coating the headlap granules produces an unexpected, beneficial result.

Although the experiments of Examples 1-3 and 9-10 used a 50/50 mixture of amido-amine and oil, other mixtures will produce comparable results. Thus, from about 10 to 90 weight percent of the oil may be mixed with from about 90 to about 10 weight percent of the amine.

In one embodiment, more than one amine antistrip agent is used. In another embodiment, more than one oil is used. In yet another embodiment, one or more non-amine antistrip agents are used. In yet another embodiment, one or more non-naphthenic oils are used.

Preparation of Headlap Granules

In one preferred process, headlap granules are prepared that have one or more of the properties described elsewhere in this specification and, in addition, contain a tinting agent that preferably comprises a pigment and a binder.

In this embodiment, the headlap granules preferably comprise at least about 0.1 weight percent of the tinting agent and, more preferably, from about 0.1 to about 0.8 weight percent of such tinting agent. In one aspect of this embodiment, the headlap granules comprise from about 0.1 to about 0.6 weight percent of the tinting agent. In another aspect of this embodiment, the headlap granules comprise from about 0.15 to about 0.45 weight percent of the tinting agent. In yet another aspect, from about 0.2 to about 0.4 weight percent of the tinting agent is present in the headlap granules.

In one aspect of this embodiment, the tinting agent is present as a coating on the surfaces of the headlap granules; preferably the coating has a thickness of from about 5 to about 15 microns.

In one embodiment, the tinting agent is comprised of from about 10 to about 35 weight percent of a pigment; in another embodiment, the tinting agent is comprised of from about 10 to about 20 weight percent of a pigment. As is known to those skilled in the art, a pigment is a substance, often in the form of a dry powder, that imparts color to another substance.

In one embodiment, the pigment is an inorganic pigment. The inorganic pigments may comprise metallic oxides (such as iron, titanium, zinc, cobalt, chromium, etc.), metal powder suspensions (gold, aluminum, etc.), earth colors (siennas, ochers, umbers, etc.), lead chromates, carbon black, etc. Reference may be had, e.g., to U.S. Pat. Nos. 3,839,064 (inorganic pigment-loaded polymeric microcapsular system), 3,925,095 (free-flowing dispersible inorganic pigment of filler compositions containing hydroxyalkylate alkylene diamines), 3,930,101 (inorganic pigment-loaded polymeric microcapsular system), 4,013,617 (process for the manufacture of hydrophilic polyolefin fibers containing inorganic pigment), 4,075,029 (inorganic pigment comprising a solid solution of differing spinels), 4,167,417 (fluorescent inorganic pigment), 4,202,702 (inorganic pigment comprising a solid solution of differing spinels), 4,269,760 (fine spherical polymer particles containing inorganic pigment and/or coloring agent and process for the preparation thereof), 4,293,478 (process for producing polyphenylene ether composition containing inorganic pigment), 4,334,933 (process for preparing stable inorganic pigment), 4,349,389 (dispersible inorganic pigment), 4,818,783 (method for production of aqueous dispersion of inorganic pigment), 5,786,436 (method of preparing inorganic pigment dispersions), 5,961,710 (inorganic pigment granules process for their production and use), 5,968,248 (heat resistant inorganic pigment), 6,197,879 (method of preparing inorganic pigment dispersions), and the like. The entire disclosure of each of these United States patents is hereby incorporated by reference into this specification.

The inorganic pigment used preferably has a particle size distribution such that at least about 95 weight percent of its particles are preferably smaller than 1 micron. In one embodiment, at least 95 weight percent of the particles of inorganic pigment have a size within the range of from about 0.1 to about 0.7 microns. In another embodiment, at least 95 weight percent of the pigment particles have a particle size within the range of from about 0.1 to about 0.5 microns.

In one preferred embodiment, the inorganic pigment is carbon black. As is known to those skilled in the art, carbon black is an amorphous powdered carbon resulting from the incomplete combustion of a gas, usually deposited by contact of the flame on a metallic surface, but also made by the incomplete combustion of gas in a chamber. Reference may be had, e.g., to pages 143-145 of George S. Brady's "Materials Handbook," Thirteenth Edition (McGraw-Hill, Inc., New York, N.Y., 1991). Reference may also be had, e.g., to U.S. Pat. Nos. 3,519,452 (sulfonated carbon black pigments), 3,725,103 (carbon black pigments), 3,799,788 (carbon black pigments), 3,836,378 (production of composite pigments or iron oxide and carbon black), 3,973,983 (carbon black pigments and rubber compositions containing the same), 4,076,551 (carbon black-containing pigments and process for their preparation), 4,170,486 (carbon black compositions and black-pigmented compositions containing same), 4,366,138 (carbon black useful for pigment for black lacquers), 4,379,871 (process for the production of carbon black containing pigment synthetic resin concentrates), 5,286,291 (pigments containing carbon black), and the like. The entire disclosure of each of these United States patents is hereby incorporated by reference into this specification.

In one embodiment, a mixture of carbon black and a resin is prepared by conventional means. The resin used is preferably a synthetic resin that, e.g., is a film-forming synthetic resin; and processes for preparing mixtures of such synthetic resin and carbon black are well known. Reference may be had, e.g., to U.S. Pat. Nos. 3,557,040 (process for preparing a carbon black-synthetic resin composition), 3,563,916 (carbon-black-synthetic resins electro-conductive composition), 3,833,541 (molding powder of aggregates containing carbon black embedded in matrix of vinyl chloride-acetate resin and heat stabilizer), 3,925,301 (process for the continuous production of carbon black-synthetic resin concentrates), 4,379,871 (process for the production of carbon black containing pigment-synthetic resin concentrates), 4,442,160 (electrostatic recording medium having an electrically conductive layer containing pre-dispersed electrically conductive carbon black and polyurethane binder resin), 4,683,158 (carpet having bottom portions of pile covered with carbon back containing resin), 4,734,450 (polypropylene-based resin composition containing an inorganic filer and 0.01 to 0.6 weight percent of carbon black), 5,041,473 (process for producing carbon black filled polyethylene resins), 5,207,949 (highly conductive polyoxymethylene resin composition containing carbon black), and the like. The entire disclosure of each of these United States patents is hereby incorporated by reference into this specification.

The tinting agent preferably contains from about 10 to about 35 weight percent of pigment (such as, e.g., carbon black), and from about 90 to about 65 weight percent of resin, both by combined weight of pigment and resin. In one embodiment, the tinting agent contains from about 10 to about 20 weight percent of pigment and from about 90 to about 80 weight percent of resin.

Figure 3:
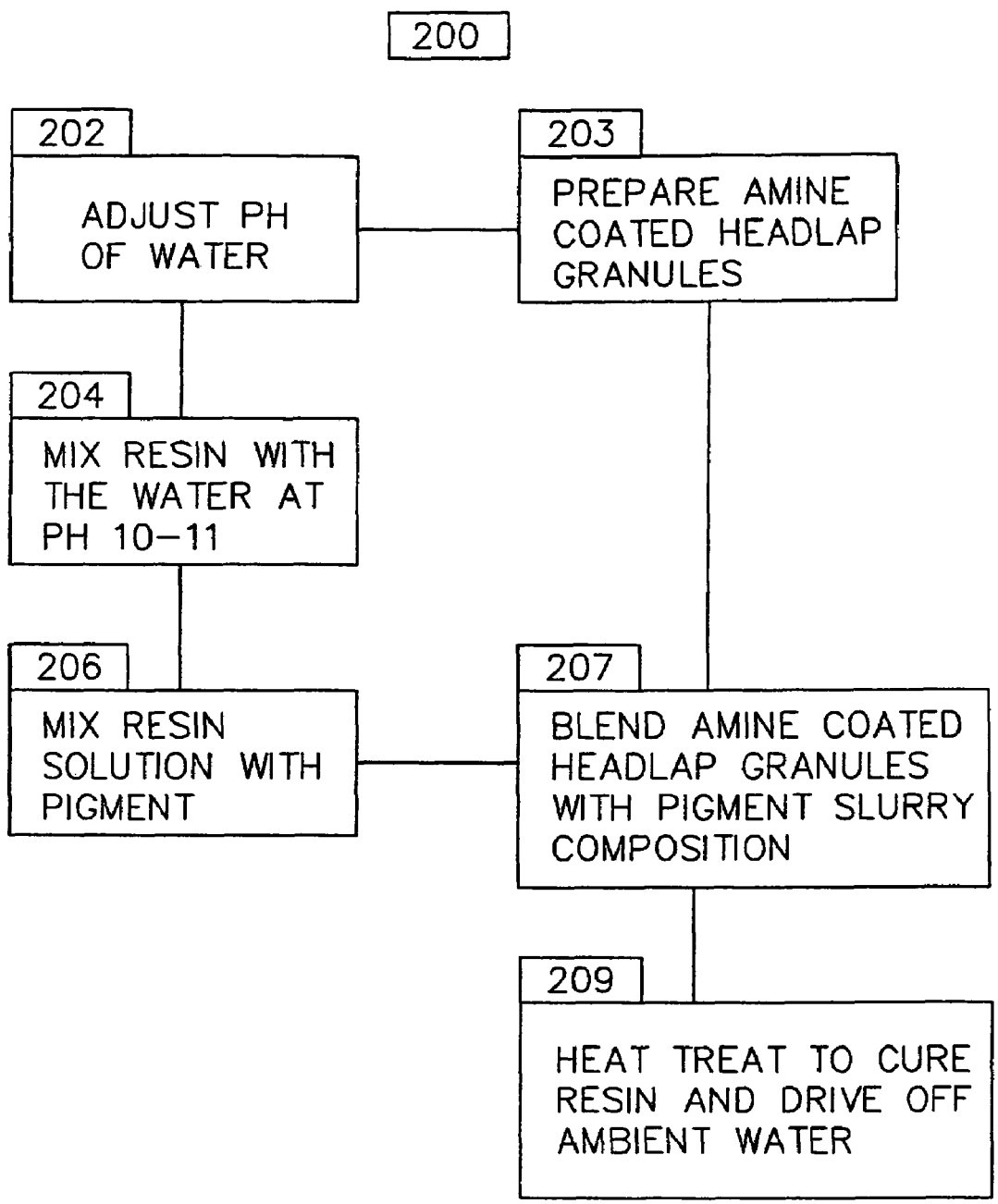
FIG. 3 is a flow diagram of another preferred process of the invention.

In one embodiment, the tinting agent is made from a water soluble resin and carbon black by the process depicted in FIG. 3. Referring to FIG. 3, and to the process 200 depicted therein, in step 202 the pH of the water used in the process is adjusted so that it is from about 10 to about 11 and, more preferably about 10.3 to about 10.7. A sufficient amount of water may be charged to a container (such as, e.g., a beaker) so that when the resin is thereafter charged to the container it will contain from about 20 to about 50 parts of resin, by total weight of resin and water.

One may add ammonia to the water to adjust its pH. Alternatively, or additionally, one may add other pH increasing agents such as, e.g., sodium hydroxide, potassium hydroxide, etc.

Once the pH of the water has been suitably adjusted, one may charge water-soluble resin to the water. One may use one or more of the water-soluble resins known to those skilled in the art. Reference may be had, e.g., to U.S. Pat. Nos. 3,420,231 (inversely water soluble resin), 3,490,039 (water soluble resin trunk polymer), 3,901,836 (rust preventative coating for metallic surfaces consisting of water-soluble resin and sodium benzoate—potassium tripolyphosphate rust inhibitor), 3,947,246 (process for producing spotted dyeings with pastes containing water-soluble resin or wax and particulate dyestuff), 4,017,433 (pitch water soluble resin and alkyd resin as binder composition for refractory particles), 4,179,417 (composition for water-based paint comprising water-soluble resin and water-dispersible polymer), 5,034,498 (method and apparatus for producing water-soluble resin and resin product made by that method), 5,039,787 (method for production of cationic water-soluble resin and water-treating agent containing said resin based on imine modified polyethylene glycol halohydrin ethers), 5,041,252 (nonwoven fabric of water-soluble resin fibers), 5,207,964 (method for manufacturing a plastic hollow product using water soluble resin), 5,264,318 (positive type photosensitive composition developable with water comprising a photocrosslinking agent, a water-soluble resin, and an aqueous synthetic resin), 5,349, 003 (aqueous fluorine-containing polymer dispersion and aqueous dispersion containing fluorine containing polymer and water-soluble resin and/or water dispersible resin), 5,360, 860 (water-soluble resin emulsion and process for preparation thereof), 5,913,972 (aqueous pigment dispersion, water-soluble resin, production process of the resin, and equipment suitable for use with the dispersion), 6,555,607 (water-soluble resin composition), 6,608,121 (water soluble resin composition and water-soluble film), 6,613,388 (method of producing a recording sheet containing inorganic particulates and a water-soluble resin), 6,720,367 (ink composition comprising cationic, water-soluble resin), 6,809,128 (ink composition comprising cationic water-soluble resin and ink set), 7,937,956 (water-soluble resin, process for its production, and water-soluble resin composition), and the like. The entire disclosure of each of these United States patents is hereby incorporated by reference into this specification.

In one embodiment, the water-soluble resin is curable and, after being so cured, becomes water insoluble. Curable resins and well known to those skilled in the art. Reference may be had, e.g., to U.S. Pat. Nos. 3,373,812 (method of permeably consolidating incompetent sands with a heat-curable resin), 4,087,479 (heat curable resin compositions for powder paints), 4,242,475 (process for producing novel curable resin capable of being cured by the exposure to heat or radiation and curable coating composition containing said curable resin), 4,528,363 (heat-curable resin coating composition), 4,861,672 (one-can heat-curable resin compositions), 4,940, 740 (single phase toughened heat-curable resin compositions), 4,985,509 (heat curable resin composition), 4,996,267 (heat-curable resin mixture of monocyanate, polycyanate, and reactive thermoplastic), 5,326,827 (heat-curable resin composition containing acrylic polymer having alicyclic epoxide functions), 5,747,615 (slurry-mixed heat-curable resin systems having superior tack and drape), 7,098,258 (heat-curable resin composition), and the like. The entire disclosure of each of these United States patents is hereby incorporated by reference into this specification.

In one embodiment, the resin used is an ester of pentaerythritol and rosin. These esters are well known and are disclosed, e.g., in U.S. Pat. No. 4,548,746, the entire disclosure of which is hereby incorporated by reference into this specification. This patent claims (in claim 1 thereof) "A process for esterifying rosin with at least an equivalent of pentaerythritol which comprises heating the rosin and pentaerythritol in the presence of phosphinic acid catalyst." This patent discloses that: "Rosin is mainly a mixture of C20, fused-ring, monocarboxylic acids, typified by levopimaric and abietic acids, both of which are susceptible to numerous chemical transformations. The rosins to which this invention relates include gum rosin, wood rosin and tall oil rosin."

U.S. Pat. No. 4,548,746 also discloses that: "The natural separation and gradual conversion of some of the hydrophilic components of sap and related plant fluids from the cambium layer of a tree into increasingly hydrophobic solids are the generic process of forming diverse gums, resins and waxes. The oleoresin intermediate in this process is typified in pine gum, which flows from hacks on the trunks of southern yellow pine in southeastern United States, in France, and in other countries. Pine gum contains about 80% (gum) rosin and about 20% turpentine."

U.S. Pat. No. 4,548,746 also discloses that: "Resinification from oleoresin can result from either natural evaporation of oil from an extrudate or slow collection in ducts in sapwood and heartwood. Pinus stumps are valuable enough to be harvested, chipped, and extracted with hexane or higher-boiling paraffins to yield wood rosin, wood turpentine, and other terpene-related compounds by fractional distillation. In the kraft, i.e., sulfate, pulping process for making paper, pinewood is digested with alkali producing crude tall oil and crude sulfate turpentine as by-products. Fractionation of the crude tall oil yields tall oil rosin and fatty acids."

U.S. Pat. No. 4,548,746 also discloses that: "The chemical transformation of gum, wood, and tall oil rosin which relates to this invention is esterification. The beneficial product characteristics provided by rosin esterification for various applications have led to the development of many esterification procedures, particularly treatments with polyhydric alcohols. U.S. Pat. Nos. 2,369,125, 2,590,910 and 2,572,086 teach rosin esterification with glycerol and pentaerythritol, among other polyhydric alcohols, usually preceded by a rosin disproportionation step."

U.S. Pat. No. 4,548,746 also discloses that: "It is generally known in the art that a significant disadvantage of pentaerythritol esterification of tall oil rosin as compared with glycerol esterification of rosin color in the product of the former process. For a tall oil rosin with a starting color of 8 on the Gardner scale, a pentaerythritol ester would have a color of 13-18 while a glycerol ester would have a color of 8-9. Also, extremely long reaction times are required to make the tall oil rosin-pentaerythritol esters (up to 30-48 hours) as compared to making tall oil rosin-glycerol esters under identical conditions (10-12 hours). It was this concern which led to the discovery of the invention process hereinafter claimed."

U.S. Pat. No. 4,548,746 also discloses that: "U.S. Pat. Nos. 3,780,012 and 3,780,013 acknowledge that tall oil rosin, as opposed to gum or wood rosin, darkens significantly upon pentaerythritol esterification and propose alternative solutions. U.S. Pat. No. 3,780,012 teaches pretreating the rosin with paraformaldehyde followed by distillation prior to the esterification reaction. U.S. Pat. No. 3,780,013 teaches the incremental addition of a phenol sulfide compound during the esterification. The color of the product of these procedures was claimed to be an M (U.S.D.A. scale), equal to 11-12 on the Gardner scale. Also, the patents' examples employed a 20% equivalent excess of pentaerythritol."

U.S. Pat. No. 4,548,746 also discloses that: "U.S. Pat. No. 2,729,660 also acknowledges the darkening effect which common esterification catalysts such as strong acids cause on the product during esterification. The patent teaches the use of 0.5 to 5% of either the aliphatic or aromatic esters of phosphorous acid as a catalyst for the esterification of higher fatty acids or rosin acids, or mixtures thereof. In addition to avoiding appreciable color formation during the esterification, a reduction in reaction time is noted. A distinct disadvantage of this process is the dissociation, during esterification, of the alcohol used to make the phosphite ester catalyst resulting in a disagreeable odor."

U.S. Pat. No. 4,548,746 also discloses that: "U.S. Pat. No. 4,172,070 teaches employing arylsulfonic acid in place of the traditional basic esterification catalysts, such as calcium oxide, to reduce the time for tall oil rosin-pentaerythritol esterification to obtain a rosin ester of improved oxygen stability, color and softening point. This work is confounded, however, by the unusually large amount of pentaerythritol used (35% equivalent excess) which by itself would markedly increase the rate of acid number drop. Products with Ring and Ball softening points of 77° C. to 86.5° C. were obtained. Normal commercial pentaerythritol esters of rosins soften between 95° C. and 105° C."

In one preferred embodiment, the resin used in a fumaric modified pentarythritol ester identified by Chemical Abstracts Registry number 68152-57-8 and sold as "Filtrez 521" by Hexion Specialty Chemicals Inc. of 1202 East Parker Street, Baxley, Ga. 31513.

Referring again to FIG. 3, and to step 204 thereof, the water-soluble curable resin is mixed with the water until it is completely dissolved. In one embodiment, from about 20 to about 50 parts of resin are mixed with about 80 to about 50 parts of water, both by weight. In another embodiment, from about 25 to about 40 parts of resin are mixed with from about 785 to about 60 parts of water. In yet another embodiment, about 30 parts of resin are mixed with about 70 parts of water.

The water used is preferably at ambient temperature, and the resin is added to the water, with stirring, and blended over a suitable period of, e.g., from about 10 to about 15 minutes. Thereafter, the solution this produced is mixed with the pigment to form a slurry. The pigment (such as, e.g., carbon black) is preferably slowly added and blended with the solution in step 206 until a substantially homogeneous slurry has been produced.

The substantially homogeneous slurry produced in step 206 is then blended with amine-coated headlap granules prepared in step 203.

In one embodiment, the amine-coated headlap granules are prepared in accordance with the process described elsewhere in this specification in which one or more of the amines described is sprayed onto the limestone granules as such granules are being transferred through a blending screw. However, in this embodiment, wherein the amine-coated headlap granules are to be mixed with the slurry, it is preferred not to use oil to during the coating of such amines onto the limestone granules.

Referring again to FIG. 3, and to the preferred embodiment depicted therein, in step 207 the amine-coated limestone granules are coated with the slurry produced in step 206. It is preferred to coat the amine-coated limestone granules with slurry in the same manner (described elsewhere in this specification) in which the uncoated limestone granules were coated with amine, viz.—spraying the coating agent (in this case the slurry, in the prior case the amine) onto the limestone granules as such granules are being transferred through a blending screw. Alternatively, or additionally, other conventional coating processes may be used; thus, e.g., a nebulizing spray mixer may be used.

The slurry-coated and amine-coated limestone granules are then heat treated in step 209, wherein they are subjected to a temperature of 130 degrees Centigrade for at least 15 minutes to drive off the water and to cure the tinting agent slurry. The product thus produced is substantially water insoluble.

The solubility of the product produced in step 209 of FIG. 3 may be tested in accordance with a process in which 100 grams of such product are disposed in a 500 milliliter beaker to which 375 milliliters of water are then added, and the material is mixed and thereafter boiled for 2 hours. Thereafter, the material is inspected to determine the extent to which, if any, the tinting agent has been removed from the limestone granules. Any of the ink that has separated from the particles will produce turbidity in the water and/or floating black particles in the water and/or material stuck to the surface(s) of the beaker. It is preferred that less than about 5 weight percent (and, more preferably, less than about 1 weight percent) of the tinting agent be removed from the coated headlap granules by this test.

Another Preferred Process of the Invention

In one embodiment, the roofing granules of this invention are made in substantial accordance with the procedure described with reference to FIGS. 1 and 3, with several modifications.

In the first place, two mixers are used (see, e.g., "mixer 44" and "mixer 45" depicted in FIG. 1). It is preferred to charge the particles from air flow separator 34 to pigment and binder mixture described in this specification. In this embodiment, the antistrip agent and/or the oil are not charged to mixer 44 but are thereafter charged to mixer 45. Thus, the difference in this new embodiment is that the pigment and binder mixture are charged and mixed with the particles prior to the time they are contacted with either the antistrip agent and/or the oil.

In one aspect of this embodiment, the mixer 44 is heated such that, during the mixing of the particles with the pigment/binder mixture, such particles are preferably heated to a temperature of at least about 130 degrees Celsius for at least about 15 minutes. In one aspect of this embodiment, such particles are heated to a temperature of at least about 130 degrees Celsius for at least about 22 minutes.

In this embodiment, one may use the same pigments and/or binders as has been described elsewhere in this specification. Alternatively, one may replace some or all of the binder described hereinbefore with a film forming binder.

As is known to those skilled in the art, a film forming binder is a material that forms a polymeric surface which encapsulates the particles with which it is contact. Reference may be had, e.g., to U.S. Pat. Nos. 5,079,037 (resistive films comprising resistive short fibers in insulating film forming binder), 5,516,458 (coating composition containing film forming binder), and 6,096,835 (coating composition containing film forming binder). Reference also may be had to published United States patent applications US2003/013050 (coating composition containing polythiophene and film-forming binder) and US2005/0029496. The entire disclosure of each of such United States patents and published United States patent applications is hereby incorporated by reference into this specification.

In one embodiment, the mineral composition of this invention is coated with a film forming binder containing a pigment. The desired effect of this pigment-binder system is to coat the exposed surface of the granules where as the cured coating surface is not readily stripped away by additional processing or by heating during processing.

When such film forming binder is used, it is preferred that to mix such binder with the pigment described elsewhere in this specification to produce a mixture that preferably comprises from about 15 to about 20 weight percent of such binder, from about 15 to about 20 weight percent of such pigment, and one or more solvents. The solvent used is preferably an aqueous solvent that comprises water.

In one embodiment, a pigment is used to produces a black color with certain L*a*b* values. These L*a*b* values may be measured using the "Lab color space system."

As is known to those skilled in the art, "Lab" is the abbreviated name of two different color spaces, the best known of which is "CIELAB" (also referred to as "CIE 1976 L*a*b*"). Both of these spaces are derived from the "master" space, CIE 1931 color space. CIELAB is calculated using cube roots, and Hunter Lab is calculated using square roots. Reference may be had, e.g. to a web site appearing at http://en.wikipedia.org/wiki/Lab_color_space.

CIELAB has been widely described in the patent literature. Thus, e.g., it is described in both the claims and the disclosures of U.S. Pat. Nos. 5,751,484 (coatings on glass), 5,932, 502 (low transmittance glass), 5,512,521 (cobalt-free, black, dual purpose enamel glass), 6,629,792 (thermal transfer ribbon with a frosting ink layer), 6,722,271 (ceramic decal assembly), 6,796,733, etc.; the disclosure of each of these United States patents is hereby incorporated by reference into this specification.

with an L value of from about 15 to about 25, an a* value of from −0.5 to 1, and a b* value of from 0 to 1. As is known to those skilled in the art, these are "Hunter L, a*, b*" colors as measured by a Hunter colorimeter. Reference may be had, e.g., to International Publication No. WO 97/45607, the entire disclosure of which is hereby incorporated by reference into this specification; (see, e.g., page 11 thereof and Table 3). Reference may also be had, e.g., an article by R. S. Hunter, "Photoelectric Color Difference Meter," Journal of the Optical Society of America, 48, 985-995 (1958). Reference may also be had to A.S.T.M. Standard Test D-6290.

In one aspect of this embodiment, the pigment used in applicants' process is carbon black, and the L* number obtained for the pigmented material obtained is less than 30. In one aspect of this embodiment, the L* value obtained is from about 15 to about 30.

It is preferred that the Hunter a* and be values be less than about 5 and, preferably, less than about 2. In one embodiment, the Hunter a* value is from about −5 to +5, and the Hunter b* value of from about −5 to about 5.

Referring again to FIG. 1, the binder, pigment, and water are preferably present in the form of an aqueous slurry, and such slurry is preferably sprayed onto the particles in mixer 44. In one embodiment, the mixer 44 preferably is comprised of nozzles through which the slurry may be sprayed as the particles are being tumbled.

During the tumbling/spraying process, it is preferred to subject the particles being so treated to a temperature of at least 130 degrees Celsius. It is also preferred to conduct the spraying operation so that a substantially homogeneous mixture of coated particles is produced. In one embodiment, the spraying, tumbling, and heating operations occur simultaneously for a period of at least 15 minutes.

In one embodiment, the coating produced on the particles, after drying, is applied at a coating weight of from about 0.25 to about 0.4 weight percent, by weight of uncoated particles.

Referring to FIG. 1, after the coated particles are prepared in mixer 44, they are then fed via line 50 to mixer 45, wherein the antistrip agent and/or the oil may be added in the manner described elsewhere in this specification. Thereafter, the treated particles may be fed via line 51 to mass flow silo 52.

The particles conveyed to mass flow silo 52 are suitable for use as headlap granules. Additionally, because of their low translucency and their optical properties, they may also be used as prime granules. As is known to those skilled in the art, "Often, in the manufacture of shingles, at least two types of granules are employed: 1) headlap granules which are granules of relatively low cost for portions of the shingle which are to be covered up; and 2) prime granules which are granules of relatively higher cost and are applied to the portions of the shingle which will be exposed on the roof. It is to be understood that the term "prime" granules generally includes both highlighted colored blend drop granules and background granules." This quote is taken from published United States patent application US2007/0082126, the entire disclosure of which is hereby incorporated by reference into this specification.

In one embodiment, the coated particles of this invention are comprised of a multiplicity of crystallites that, when contacted with daylight, produce electromagnetic energy that is lethal to algae. In one aspect of this embodiment, such crystallites are comprised or consist essentially of inorganic material.

Claims Presented in Applicant's International Patent Application PCT/US06/22389.

Applicant has presented certain claims in his International patent application PCT/US06/22789, the entire disclosure of which is hereby incorporated by reference into this specification. Claim 1 of such patent application describes: "1. A mineral composition comprised of at least about 90 weight percent of headlap granules, at least about 50 weight percent of calcium carbonate, less than about 100 parts per million of a metal selected from the group consisting of arsenic, barium, cadmium, chromium, lead, mercury, selenium, and silver and less than about 100 parts per million of a polycyclic aromatic hydrocarbon, wherein said mineral composition, when tested in accordance with by ASTM Standard Test D 4977-03, loses less than 5 grams of material.

While preferred embodiments of the invention have been shown and described, modifications thereof can be made by one skilled in the art without departing from the scope of and the spirit of the invention. The embodiments described herein are exemplary and not limiting. Many variations thereof are possible and are within the scope of the invention

We claim:

1. A mineral composition comprised of at least 90 weight percent of roofing granules, wherein said roofing granules are comprised of at least about 95 weight percent of calcium carbonate with a hardgrove grindability index of less than about 70, and from about 0.1 to about 1.0 weight percent of a pigmented material, wherein said pigmented material is comprised of from about 10 to about 35 weight percent of pigment and from about 90 to about 65 weight percent of a resin, and wherein:

(a) said roofing granules are comprised of amine antistrip agent;
(b) at least 80 weight percent of said roofing granules have sizes in the range of from about 600 to about 1400 microns;
(c) less than about 4 weight percent of said roofing granules are smaller than 250 microns;
(d) said roofing granules are comprised of at least 95 weight percent of particles smaller than 1700 microns;
(e) said roofing granules are comprised of at least 30 weight percent of particles smaller than 850 microns; and
(f) said roofing granules are comprised of at least 3 weight percent of particles smaller than 600 microns.

2. The mineral composition as recited in claim 1, wherein said resin is a film-forming resin.

3. The mineral composition as recited in claim 1, wherein said resin is a synthetic resin.

4. The mineral composition as recited in claim 1, wherein said pigmented material is comprised of from about 10 to about 20 weight percent of said pigment.

* * * * *